US012758549B2

(12) United States Patent
Winckle et al.

(10) Patent No.: US 12,758,549 B2
(45) Date of Patent: Oct. 13, 2026

(54) HYDROGEL COMPOSITION AND USES THEREOF IN THE PREVENTION AND/OR TREATMENT OF SKIN DAMAGE CAUSED BY RADIATION

(71) Applicant: TARIAN PHARMA, Grasse (FR)

(72) Inventors: Gareth Winckle, Juan les Pins (FR); Philippe Andres, Peymeinade (FR); Janusz Czernielewski, Vallauris (FR)

(73) Assignee: TARIAN PHARMA, Grasse (FR)

( * ) Notice: Subject to any disclaimer, the term of this patent is extended or adjusted under 35 U.S.C. 154(b) by 480 days.

(21) Appl. No.: 18/264,286

(22) PCT Filed: Feb. 18, 2022

(86) PCT No.: PCT/EP2022/054037
§ 371 (c)(1),
(2) Date: Aug. 4, 2023

(87) PCT Pub. No.: WO2022/175428
PCT Pub. Date: Aug. 25, 2022

(65) Prior Publication Data

US 2024/0100044 A1 Mar. 28, 2024

(30) Foreign Application Priority Data

Feb. 19, 2021 (FR) ....................................... 2101620

(51) Int. Cl.

| | |
|---|---|
| ***A61K 31/498*** | (2006.01) |
| ***A61K 9/00*** | (2006.01) |
| ***A61K 9/06*** | (2006.01) |
| ***A61K 47/10*** | (2017.01) |
| ***A61K 47/20*** | (2006.01) |
| ***A61K 47/22*** | (2006.01) |
| ***A61K 47/32*** | (2006.01) |
| ***A61K 47/36*** | (2006.01) |
| ***A61P 17/00*** | (2006.01) |

(52) U.S. Cl.
CPC .......... *A61K 31/498* (2013.01); *A61K 9/0014* (2013.01); *A61K 9/06* (2013.01); *A61K 47/10* (2013.01); *A61K 47/20* (2013.01); *A61K 47/22* (2013.01); *A61K 47/32* (2013.01); *A61K 47/36* (2013.01); *A61P 17/00* (2018.01)

(58) Field of Classification Search
CPC ...... A61K 31/498; A61K 9/0014; A61K 9/06; A61K 47/10; A61K 47/20; A61K 47/22; A61K 47/32; A61K 47/36; A61P 7/00
See application file for complete search history.

(56) References Cited

U.S. PATENT DOCUMENTS

2015/0119401 A1 4/2015 Horn
2016/0166569 A1* 6/2016 Bouvier .................. A61P 17/12
514/249

OTHER PUBLICATIONS

English Translation of International Search Report in related Application No. PCT/EP2022/054037, Aug. 25, 2022, 2 pages.
Written Opinion of International Search Report in related Application No. PCT/EP2022/054037, Aug. 25, 2022, 7 pages.
MIRVASO 3mg/g gel brimonidine, Package leaflet: Information for the patient, May 2024, 2 pages.
Highlights of Prescribing Information, MIRVASO (brimonidine) topical gel, Jul. 2016, 10 pages.
Annex I Summary of Product Characteristics, Mirvaso 3 mg/g gel, 29 pages.

* cited by examiner

*Primary Examiner* — Zohreh A Fay
(74) *Attorney, Agent, or Firm* — FisherBroyles, LLP; Susan M. Oiler

(57) ABSTRACT

Compositions in a form suitable for topical administration, which is water-based, contain a vasoconstrictor. The vasoconstrictor is chosen from brimonidine or salts thereof, in a solvent-based phase of polyethylene glycol in combination with propylene glycol and/or dimethyl sulfoxide (DMSO), a hydrophilic film-forming agent chosen from a polyvinylpyrrolidone/vinyl acetate copolymer, polyvinylpyrrolidone in a non-crosslinked, crosslinked or acetate form, taken alone or in combination, and glycerine which is in the form of a hydrogel. Methods for prevention and/or treatment of dermatitis resulting from radiation, notably in the context of a radiotherapy treatmen, involve administering the compositions to a patient in need thereof.

17 Claims, 5 Drawing Sheets

HYDROGEL COMPOSITION AND USES THEREOF IN THE PREVENTION AND/OR TREATMENT OF SKIN DAMAGE CAUSED BY RADIATION

CROSS-REFERENCE TO RELATED APPLICATIONS

The present invention is filed under 35 U.S.C. § 371 as the U.S. national phase of International Patent Application No. PCT/EP2022/054037, filed Feb. 18, 2022, which designated the United States and which claims the benefit of French Patent Application No. 2101620, filed Feb. 19, 2021, which is hereby incorporated in its entirety including all tables, figures, and claims.

TECHNICAL FIELD

The invention relates to the field of pharmaceutical compositions in a form suitable for topical administration. It relates more particularly to a pharmaceutical composition comprising a vasoconstrictor such as brimonidine or salts thereof, as well as such a composition for use as a medicine, more particularly in the prevention and/or treatment of radiation damage to skin.

Types of radiation that can damage the skin include ultraviolet (UV), including UVA and UVB which can cause sunburn, rays in the visible range, infra-red radiation (IR), ionising radiation such as X-rays and alpha, beta or gamma radiation, and radiation composed of protons.

STATE OF THE ART

One of the first effects of radiation exposure on tissue is erythema, an inflammatory response that causes dilation of blood vessels and reddening of the skin. This reaction is visible approximately 6-8 hours after exposure to UV and disappears after 36-48 hours.

Dermal application of a highly selective alpha2-adrenergic receptor agonist to the face is known to reduce erythema by means of direct cutaneous vasoconstriction. The main characteristic of cutaneous vasoconstriction is pallor; by reducing the diameter of arterioles and small vessels in the dermis, it brings about an immediate reduction in blood flow, producing as reduction in skin colour in particular.

MIRVASO® gel (0.5% w/w brimonidine tartrate) is thus indicated for symptomatic treatment of facial erythema associated with rosacea in adults. In addition to brimonidine tartrate, this gel includes carbomer homopolymer type B, glycerine, methylparaben, phenoxyethanol, propylene glycol, sodium hydroxide, titanium dioxide and purified water.

Brimonidine is more particularly known for being a highly selective alpha2-adrenergic receptor agonist. Brimonidine is 1,000 times more selective for alpha2-adrenergic receptors than for alpha1-adrenergic receptors.

Brimonidine has been found to be useful in the treatment of erythema caused by acne rosacea, and has been proposed for other skin disorders. See for example patent application U.S. Ser. No. 10/853,585, patent application U.S. Ser. No. 10/626,037 and patent application U.S. Ser. No. 12/193,098.

Patent document US2020121675 is also known, describing a gel formulation comprising 0.3% brimonidine 0.3%, 1% benzyl alcohol, ascorbic acid, butylated hydroxyanisole, butylated hydroxytoluene, carbomer homopolymer type B, di-sodium edetate, hexylene glycol, poloxamer 407, polyethylene glycol 400, polysorbate 40, purified water and tromethamine for the treatment of rosacea.

A topical product designed for therapeutic purposes usually consists of an active agent and excipients. During formulation, the choice of excipients is essential to guarantee the efficacy of the drug by making the active agents soluble and optimising their skin penetration, for the stability of the galenical form and its texture, for local tolerance and for patient compliance. As well as the optimisation of each of these individual elements, a complex and complementary challenge is to identify the optimal balance of these key factors to deliver a product that meets the needs of patients, healthcare professionals and regulators alike.

Brimonidine (tartrate) shows a chemical stability suitable for topical administration and a solubility profile that offers various formulation options.

On the other hand, it is generally difficult to create a release and cutaneous reservoirs with ionised active agents including salts, because they tend to penetrate the stratum corneum (a barrier composed mainly of lipids) less readily. Furthermore, such active agents tend to be rapidly cleared from viable tissues due to their solubility in water.

Brimonidine is in fact a hydrophilic molecule and thus has difficulty penetrating through the lipid stratum corneum.

On the other hand, once the stratum corneum has been crossed, brimonidine enters a hydrophilic medium (the epidermis, especially the granular layer and the basal layer, and then the dermis), and is then eliminated, thus reducing effectiveness in terms of vasoconstriction.

The structure of the barrier formed by the skin thus poses a real challenge to obtaining a topical formulation designed for application to the skin, allowing the active vasoconstrictor agent to pass the outer lipid layer without being eliminated quickly in the lower hydrophilic layers in order to produce a rapid, consistent and prolonged vasoconstrictor effect for a period of 16 hours or even 24 hours.

Furthermore, the concentration of active vasoconstrictor agent used must not be too high, as it would then pose a risk of significant and potentially harmful exposure at systemic level.

In addition, certain compounds used in compositions intended for topical application may cause side effects, which could limit their use and therefore their effectiveness. For example, certain active agents have the major disadvantage of causing irritation, which can lead to poor tolerance of the product. This in turn can result in non-compliance with treatment and dissatisfaction with the said treatment, on the part of the patient.

To this end, the formulation of MIRVASO® gel with its base of methyl parahydroxybenzoate, propylene glycol, carbomer, phenoxyethanol, glycerol, titanium dioxide, sodium hydroxide and purified water is, for example, not suitable for the prevention of lesions linked to radiation; such a formulation has non-optimal pharmacokinetics with limited activity from 6-12 hours after application. In addition, it contains particles of titanium dioxide which interfere with radiation when it is used for therapeutic purposes, for example in the prevention or treatment of radiation dermatitis.

There is currently a need to develop new compositions, making it possible to limit the effects linked to radiation and in particular the side-effects of treatment of cancer by radiotherapy.

Radio-dermatitis (or radiation-induced dermatitis) produces lesions that can be painful and worrisome for the patient, and can lead to temporary or permanent discontinuation of treatment.

There is however no consensus on the treatment of acute radio-dermatitis. A number of different solutions have been proposed, currently without sufficient levels of satisfaction to be adopted by all.

For acute grade 1 radiation dermatitis, emollients applied a few hours after the radiation session (such as DEXERYL® or TOPICREME®) moisturise the skin and bring a brief sense of well-being to the patient.

However, it is important to note that this option requires these products not to be applied before the session, to avoid a bolus effect (local increase in dose of radiation) and an increased risk of burning.

Some more specific products are offered for radio-dermatitis lesions, such as creams based on hyaluronic acid, TETA® cream or BIAFINE®. It is however recalled here that these treatments have not provided proof of effectiveness and that on the contrary, clinical studies have concluded that there is no effect.

Local topical corticosteroids (such as DIPROSONE®) should also be applied after the session. The theoretical principle of using these products is to reduce the inflammation caused by radiotherapy. Although topical corticosteroids do not provide real benefits for the development of radio-dermatitis, they are effective in cases of local allergic reaction (for example in cases of eczema linked to adhesives used for marking purposes).

In cases of acute radio-dermatitis, the continuation of radiotherapy treatment can be interrupted temporarily if the radiotherapist deems it necessary or preferable, depending on the progress of the treatment and the treatment priorities.

The use of one topical vasoconstrictor, epinephrine, has been described for the prevention of radiation dermatitis in patients with breast cancer undergoing radiation therapy (James F. Cleary et al., Significant suppression of radiation dermatitis in breast cancer patients using a topically applied adrenergic vasoconstrictor, Radiation Oncology, 2017).

However, such a product, which is an extemporaneous alcohol-based preparation that evaporates, needs to be applied just before the radiotherapy treatment, up to 20 minutes before.

Moreover, its effect is limited, most notably because of its excessively short duration of action. Only 50% of patients, therefore, showed a significant benefit in the study in question.

In these cancer treatments, which patients already find difficult to tolerate, side effects can be limiting and can interfere with the optimal course of treatment. There is therefore a real need for new effective formulations that make it possible to produce a powerful and prolonged protective effect and thus substantially reduce the cutaneous side effects of radiotherapy treatment.

There is therefore a need to develop new formulations aimed at producing a powerful, prolonged, controlled reduction in blood flow in the skin over time, limited to the application site and overcoming the above-mentioned shortcomings in terms of tolerance, effectiveness and compliance for patients undergoing radiation, in particular for cancer patients being treated with radiotherapy.

Technical Problem

Considering the foregoing, one problem that the present invention proposes to solve consists in developing an optimised topical formulation based on a well-established vasoconstrictor, such as brimonidine tartrate and aimed at improving the duration and potency of activity of the vasoconstrictor in preventing and significantly reducing the main cutaneous side effects caused by radiation, most notably in the treatment of cancer by radiotherapy.

Advantages Obtained

The Applicant has developed a new topical composition which improves the duration and potency of vasoconstriction by making the vasoconstrictor bioavailable in the dermis and epidermis for longer than 12-14 hours, to protect the skin against damage caused by radiation and more particularly against the cutaneous side effects of radiotherapy treatment, while avoiding any interference with the radiotherapy rays likely to reduce their effectiveness on the tumour being treated or the radiation field.

Combinations that are complex and difficult to provide containing polar solvents of low molecular weight (below 150 g/mol and preferably below 100 g/mol) and polar solvents of higher molecular weight (above 150 g/mol, preferably between 350-650 g/mol) have been developed in order to create a vasoconstrictor reservoir on the surface of the skin and in the upper layers of the stratum corneum. However, the formation of reservoirs of hydrophilic compounds is much more complex than for lipophilic agents, as the polar compounds are not distributed in the stratum corneum as easily as lipophilic compounds. In addition, hydrophilic compounds distribute themselves more freely in viable tissues and are removed by circulation of blood into the underlying local vascular system. An optimal and complex compositional balance must therefore be identified to modulate variables such as thermodynamics, residual surface solubility, solubility in the stratum corneum, penetration and persistence in viable tissues (traction effects/solvent drag).

In addition to the parameters described above, elements important for creating acceptable dosage forms and finished products were also considered when developing the compositions according to the invention. The compositions according to the invention have been centred on optimal solvent systems which facilitate dermal administration and provide adequate physical, chemical and microbiological stability, in addition to appropriate local tolerance and cosmetic elegance.

The optimised topical composition thus proposed by the Applicant improves the duration of the vasoconstriction process (from a period of at least 14 hours to 24 hours) as well as its power, without however disrupting the passage of the radiation through the skin and thus avoiding reductions in its efficacy.

The composition according to the invention will help create a reservoir of polar-vasoconstrictor active agent in the stratum corneum, a phenomenon usually obtained only with lipophilic molecules such as corticosteroids, as polar molecules are generally "washed out" quickly by circulation of blood. This allows a level of persistence in the skin and therefore maximises and speeds up the effect during each re-application, offering flexibility of use to both patients and radiotherapists.

The optimised composition, which is particularly suitable for radiotherapy treatment, helps promote patient compliance and maximise the effectiveness of anti-cancer treatment.

Also, the new topical formulation thus developed by the Applicant is well tolerated because it irritates very little or not at all compared to the compositions of the prior art, with improved skin penetration and increased solubility of brimonidine tartrate.

Finally, the pharmaceutical compositions according to the invention developed are also economical, easy and quick to prepare.

Technical Solution

The first aim of the solution to this problem is a composition in a form suitable for topical administration, with a water base, comprising a vasoconstrictor, said vasoconstrictor being chosen from brimonidine or salts thereof, in a solvent-base phase comprising:

- polyethylene glycol in combination with propylene glycol and/or dimethyl sulfoxide (DMSO);
- a hydrophilic film-forming agent chosen from a polyvinylpyrrolidone/vinyl Acetate copolymer, polyvinylpyrrolidone (PVP) in a non-crosslinked, crosslinked or acetate form, taken alone or in combination, preferably a polyvinylpyrrolidone/vinyl Acetate copolymer as a hydrophilic film-forming agent; and
- glycerine;

the said composition being in the form of a hydrogel.

The second aim of this solution is a composition according to the invention for use as a medicine.

BRIEF DESCRIPTION OF THE DRAWINGS

The invention and the advantages deriving therefrom will be better understood by reading the following description and the non-limiting methods of implementation, in relation to the annexed figures in which.

DESCRIPTION OF EMBODIMENTS

Figure 1:
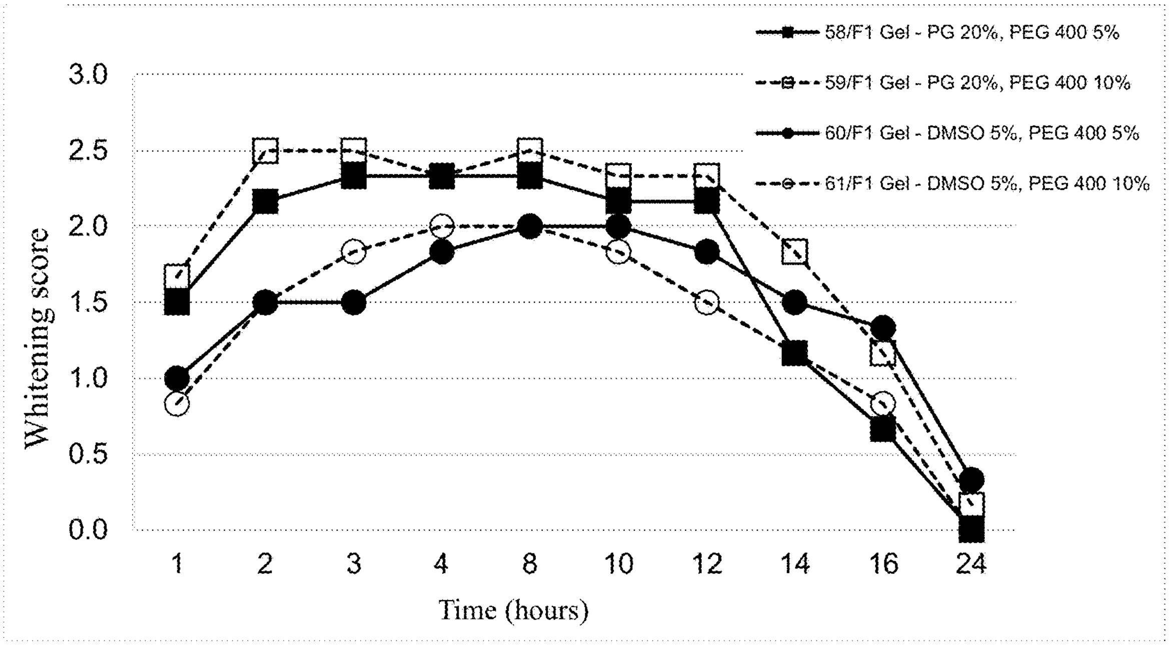
FIG. 1 represents the skin whitening scores obtained with various hydrogel compositions: 19-0155.0058/F1, 19-0155.0059/F1, 19-0155.0060/F1 and 19-0155.0061/F1.

The invention relates to a water-based composition in a form suitable for topical administration, comprising a vasoconstrictor.

The topical composition according to the invention is characterized in that it is in the form of a hydrogel.

Hydrogels are defined as hydrophilic three-dimensional polymeric matrices capable of absorbing and swelling with water without dissolving.

Typically, one limitation of hydrogels is that they are not compatible with lipophilic active agents or excipients, known for promoting skin delivery and presenting good sensory qualities, without the addition of pharmaceutically acceptable solvents which are hydrophilic in nature. However, if excessive concentrations of unsuitable polar solvents are used in the aforementioned hydrogel compositions, tolerability and organoleptic properties may be compromised.

Hydrogels are galenic forms advantageously used for topical treatment of skin diseases as they are generally very well tolerated and facilitate application of the active ingredient. These attributes are associated with high water content and the use of effective and biocompatible polymeric gelling agents.

Such a composition is advantageously suitable for delivery of hydrophilic active agents such as brimonidine, and preferentially brimonidine tartrate, and promotes penetration into the skin and permeation through the skin.

The hydrogels according to the invention are low-viscosity and can be spread easily on the application site at skin level. They allow relatively rapid absorption of the finished product while leaving minimal residue on the surface of the skin after rapid drying, with loss of feeling of residue less than 10 minutes, advantageously less than 5 minutes, more advantageously less than 2 minutes, and even more advantageously less than one minute, after application.

The topical compositions according to the inventions have a viscosity between 50 cps and 3000 cps, preferably between 300 cps and 2800 cps, for example 500 cps, 1000 cps, 1500 cps, 1600 cps, 1700 cps, 1800 cps, 2000 cps, 2500 cps or 2750 cps.

The hydrogels according to the invention also provide a moisturising sensation thanks to a high water and glycol content and to the possibility of using polymers to modulate water retention and prolonged solubilisation of the active agent on the skin surface, and thus extend the duration of effectiveness of vasoconstriction following application to the skin.

The topical composition according to the invention is characterised in that it comprises a vasoconstrictor chosen from brimonidine or salts thereof, in a solvent-base phase comprising:

- polyethylene glycol in combination with propylene glycol and/or dimethyl sulfoxide (DMSO);
- a hydrophilic film-forming agent chosen from a polyvinylpyrrolidone/vinyl acetate copolymer (KOLLIDON VA 64®), polyvinylpyrrolidone (PVP) in a non-crosslinked, crosslinked or acetate form, taken alone or in combination, preferably a polyvinylpyrrolidone/vinyl acetate copolymer as a hydrophilic film-forming agent; and glycerine.

The term “salts or pharmaceutically acceptable salts” refers to those salts of a compound of interest that are safe and effective for topical use in mammals and that possess a desired biological activity. Pharmaceutically acceptable salts include salts of acid or base groups present in the specified compounds. Pharmaceutically acceptable acid addition salts include, but are not limited to the following: salts of hydrochloride, hydrobromide, hydriodide, nitrate, sulphate, bisulphate, phosphate, acid phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulphonate, ethanesulphonate, benzenesulphonate, p-toluenesulphonate and pamoate (that is, 1,1'-methylene-bis-(2-hydroxy-3-naphthoate)). Certain compounds used in the present invention can form pharmaceutically acceptable salts with various amino acids. Suitable base salts include, but are not limited to, salts of aluminium, calcium, lithium, magnesium, potassium, sodium, zinc and diethanolamine. For a review of pharmaceutically acceptable salts, see Berge et al., 66 J. PHARM. SCI. 1-19 (1977). In the present context, the term “hydrate” refers to a compound of interest, or a pharmaceutically acceptable salt thereof, which further comprises a stoichiometric or non-stoichiometric amount of water bound thereto by non-covalent intermolecular forces.

Preferably, the brimonidine used in the compositions according to the invention is brimonidine tartrate, although the salt form presents a challenge from a stability point of view for a hydrogel formulation.

Indeed, the salts can interact with non-ionic surfactants and polymers and reduce their aqueous solubility and thus harm the physical stability of the semi-solid formulation. Conversely, the salt form of the active agent generates a relatively high aqueous solubility and advantageously allows the design and evaluation of aqueous-based formulations, which can offer improved performance in terms of sensory and local tolerance.

Preferably, concentrations of between 0.15% and 3.00% of brimonidine or salts thereof, preferably brimonidine tartrate, by weight of the total weight of the composition are preferably used to obtain the effectiveness and an improved duration of the effect until 24 hours after application while preventing any risk of systemic exposure.

Preferably, the composition according to the invention comprises brimonidine or salts thereof, preferably brimonidine tartrate, at a concentration between 0.50% and 2.50% by weight of the total weight of the composition, preferably between 0.75% and 1.50% w/w, more preferably between 1.00% and 1.50% w/w, and even more preferably 1.00% or 1.50% w/w.

The concentration of brimonidine, preferably of brimonidine tartrate, and the dose thus applied, is advantageously adapted according to the place of application.

Indeed, the barrier formed by the skin is thicker, in particular in terms of the stratum corneum to be passed through, on the feet and hands than on the scalp, with the rest of the body and in particular the chest having an intermediate thickness. For the same dose, therefore, the concentration preferably used is advantageously lower on the scalp, for example in the region of 0.15-0.5% w/w, compared to that used on the rest of the body, for example the chest with a concentration of 0.75-1.5% w/w, or even on the feet and hands, for example 1.5-3% w/w.

The topical composition according to the invention is characterized in that it comprises polyethylene glycol (PEG) in combination with propylene glycol and/or dimethyl sulfoxide (DMSO).

Although low-molecular-weight polyethylene glycols (PEGs) are commonly used in topical products, primarily because they are generally effective solvents for many types of active ingredients, they are not necessarily the most effective excipients in terms of topical administration.

This is essentially because of their polarity and high molecular weights, which limit their absorption by the skin. These properties limit the vehicle potential of the solvent (traction effect) of the active agent in the skin. This usually occurs when a solvent dissolves in the skin and carries the dissolved solute into the skin.

In addition, the high solubilising capacity of PEGs can lead to suboptimal thermodynamics for topical administration, and in cases of use at high concentrations, product transformation, often associated with evaporation of volatile components such as water, cannot be used to enhance release in the skin. When viewed holistically, these properties can reduce delivery efficiency, although high concentrations are possible; most of the applied dose of topical agents remains on the surface of the skin or is lost to the surroundings by contact transfer.

Increased delivery efficiency, fraction of the applied dose, may limit the need for increased doses to achieve targeted levels of dermal delivery and the need to use high PEG concentrations.

It has also been shown that the penetration and permeation of PEGs depends on their molecular weight.

Nevertheless, in the hydrogel compositions according to the invention, PEGs are essential for the topical formulation.

PEGs with low molecular weights up to PEG-600, such as PEG-200, PEG-300, PEG-400 or even PEG-400 SR, are preferentially used, more preferentially PEG-400 and even more preferentially PEG-400 SR advantageously promoting stability and tolerance of the hydrogel composition according to the invention by limiting the potential for irritation, eliminating polar impurities and thus reducing the interaction between excipient and active agent (brimonidine tartrate) and subsequent degradation of the active agent.

Although PEG-400 or PEG-400 SR exhibits relatively low penetration into the stratum corneum due to its molecular weight and high polarity (low partition coefficient), it is the preferentially-used PEG in the hydrogel composition according to the invention to reduce the rate of precipitation of the active agent on the skin surface and in the upper layers of the stratum corneum, for surface solubilisation. This promotes sustained delivery of brimonidine tartrate into viable layers of the skin and specifically into the vessels of the dermal plexus where the target site for the brimonidine tartrate is located. PEG-400 or PEG-400 SR has adequate solubility to promote better retention of brimonidine tartrate in solution on the skin surface and in the upper layers of the stratum corneum.

Preferably, the composition according to the invention comprises PEG at a concentration of between 1% and 20% by weight of the total composition weight, preferably between 5% and 15%, more preferably 10%.

Propylene glycol (PG, 1,2-propanediol) is a clear, colourless and hygroscopic liquid widely used as a solvent and preservative in a variety of parenteral and non-parenteral pharmaceutical formulations.

PG is known to be a better general solvent than glycerine and dissolves a wide variety of materials including corticosteroids, phenols, barbiturates, vitamins (A and D), most alkaloids and many local anaesthetics.

However, in the case of brimonidine tartrate, PG shows 50% of the solubilising capacity of glycerine.

As an antibacterial agent, PG possesses an effect similar to that of ethanol; however, it is slightly less effective against mould, with a profile comparable to that of glycerine.

PG also exhibits some volatility: although a fraction of the applied dose evaporates when applied to the skin or at least within 37 hours of application, a much larger portion penetrates the stratum corneum and penetrates into the deeper layers of the skin.

The relatively rapid penetration of PG through the stratum corneum, and its volatility, can deplete the residual vehicle of its solvent, increase the thermodynamic activity of the active agent in the vehicle, and thus modify the driving force of diffusion. In addition, PG penetration and permeation can also disrupt the lipid barrier in the stratum corneum and consequently reduce diffusional resistance.

PG therefore possesses favourable physical and chemical properties in terms of skin penetration and permeation and is absorbed through the skin. Therefore, solutes that are readily dissolved by PG (that is, have high solvent/vehicle affinity) may advantageously benefit from enhanced skin penetration via a solvent resistance mechanism or effects of traction.

Even though data for various compounds are described in the literature as indicating that dermal delivery of pharmaceutically relevant compounds can be enhanced by PG, it is not obvious for those skilled in the art to predict these characteristics in terms of stability, permeation efficiency of active agent especially with brimonidine tartrate, and tolerability when it is used in a complex solvent system to obtain topical compositions according to the invention that are effective, stable and pharmaceutically acceptable.

A fortiori, PG is known to penetrate the skin more rapidly than most active agents and that therefore, precipitation of the active agent on the surface of the skin will limit its duration of action.

In addition, the concentrations of PG used in vivo are generally limited to about 20% w/w or less, to avoid local irritation reactions and problems of systemic toxicity.

The choice to use PG as a solvent and penetration enhancer in topical compositions according to the invention is not easily predictable, due to solubility and other vehicle-related variables.

Preferably, the composition according to the invention comprises PG at a concentration of between 5% and 40% by weight of the total composition weight, preferably between 10% and 30%, more preferably between 15% and 25%, and even more preferably 20%.

Dimethyl sulfoxide (DMSO) is a colourless, odourless, water-miscible and hygroscopic aprotic solvent. It is known for its abilities to dissolve many small polar and non-polar molecules in addition to several polymeric agents, and as an agent that facilitates the penetration of hydrophilic and lipophilic compounds, including antiviral agents, steroids and antibiotics.

Several potential mechanisms for skin penetration have been described for DMSO, including:

- modification of the inter-cellular conformation of keratin, from the helical form to a β (beta) sheet,
- displacement of bound water from keratin,
- extraction of skin lipids,
- interaction with the lipid groups of the polar head, resulting in lipid fluidity and reduced diffusional resistance,
- interaction with lipid alkyl chains in the stratum corneum,
- increased distribution of the vehicle in the stratum corneum via increased solubility of permeants in the aqueous domain between the lipid bilayers.

It is well known that DMSO easily penetrates and impregnates the skin.

Surprisingly, DMSO can also produce a solvent trail effect in terms of delivery of active agent through the skin.

The effects of DMSO depend on its concentration level. Generally speaking, co-solvent systems containing a DMSO concentration greater than 60% w/w produce optimal efficiency.

However, these relatively high concentrations of DMSO can most notably cause erythema and irritation.

These factors limit the use of DMSO in topical and transdermal compositions at high concentrations.

At a lower concentration, DMSO can be used as an active solubiliser in the stratum corneum, for example at a concentration of 45% in the topical analgesic product PENNSAID®.

In the compositions according to the invention, DMSO is preferably used at a limited concentration compared to the compositions of the aforementioned prior art, less than 20% w/w, preferably less than 10% w/w and more preferably in the region of 5% w/w.

Advantageously, the relatively high solubility of brimonidine tartrate in DMSO, coupled with a limited concentration, make it a preferred solvent for the compositions according to the invention.

It is particularly advantageous, in the context of the hydrogel compositions according to the invention, to control the PEG:PG and/or PEG:DMSO ratio.

Concentrations that are too high for association of PEG in combination with PG and/or DMSO, and greater than 50% w/w, have negative effects in terms of intensity of vasoconstriction of brimonidine tartrate.

According to one preferred embodiment, PEG and PG are used in a ratio of 1:1 to 1:5 and preferably 1:2.

According to one preferred embodiment, PEG and DMSO are used in a ratio of 1:1 to 5:1, preferably 2:1.

According to a particular preferred embodiment of hydrogel compositions according to the invention, PEG is taken in combination with PG only, more preferably a combination of PEG-400 SR and PG.

Preferably, the composition according to the invention comprises polyethylene glycol (PEG) at a concentration of 10% by weight of the total weight of the composition, in combination with propylene glycol (PG) at a concentration of 20% by weight of the total weight of composition.

The topical composition according to the invention is characterized in that it comprises a hydrophilic film-forming agent chosen from a polyvinylpyrrolidone/vinyl acetate copolymer, polyvinylpyrrolidone (PVP) in a non-cross-linked, crosslinked or acetate form, taken alone or in combination.

Preferably, the composition according to the invention comprises the hydrophilic film-forming agent, taken alone or in combination, at a concentration of between 0.1% and 1.5% by weight of the total weight of the composition, preferably between 0, 25% and 1.4%, more preferably between 0.5% and 1.3%, even more preferably between 0.75% and 1.25%, and even more preferably at 1%.

Preferably, the topical composition according to the invention comprises a polyvinylpyrrolidone/vinyl Acetate copolymer (KOLLIDON VA 64®) as a hydrophilic film-forming agent.

Preferably, the composition according to the invention comprises the polyvinylpyrrolidone/vinyl acetate (KOLLI- DON VA 64®) copolymer at a concentration of between 0.1% and 1.5% by weight of the total weight of the composition, preferably between 0.25% and 1.4%, more preferably between 0.5% and 1.3%, more preferably between 0.75 and 1.25, and even more preferably at 1%.

The topical composition according to the invention is characterized in that it further comprises glycerine.

Glycerine (glycerol) is a well-known humectant that can increase water retention in the stratum corneum and improve hydration.

Glycerine is also known and used to support the normal functioning of the skin barrier, promote skin elasticity and plasticity, improve skin smoothness and provide anti-irritant effects. Glycerine is in fact able to attract water into the stratum corneum from the epidermis and the atmosphere.

Due to its relatively high polarity, glycerine does not penetrate the skin to the same degree and depth as propylene glycol, but it can accumulate and form a reservoir in the hydrophilic regions of the stratum corneum and increase the water content.

The interaction of glycerine with the stratum corneum, its distribution in the skin, and its relatively high solubility for brimonidine tartrate (twice that of propylene glycol) provide advantages in terms of improved delivery to and prolonged penetration of the skin, without causing stickiness on the skin surface.

Preferably, the composition according to the invention comprises glycerine at a concentration between 1% and 20% by weight of the total weight of the composition, preferably between 2% and 15%, more preferably between 3% and 10%, and even more preferably at 4%.

In a particularly advantageous way, the combination of PG and glycerine improves the distribution of the active agent, preferentially brimonidine tartrate, within the stratum corneum.

Additionally, and advantageously, DMSO provides a similar function to PG but with higher solubility for brimonidine tartrate. This solubility differential is an advantage for administering the product through the skin.

Preferably, the topical composition according to the invention further comprises a gelling agent chosen from xanthan gum or hydroxyethylcellulose (HEC), taken alone or in combination; more preferably, the topical composition according to the invention comprises at least xanthan gum as a gelling agent.

Preferably, the composition according to the invention comprises xanthan gum and/or HEC at a concentration between 0.1% and 1.5% by weight of the total weight of the composition, preferably between 0.2% and 1%, more preferably between 0.2% and 0.75%, and even more preferably at 0.2-0.5% for xanthan gum and 0.3-0.5% for HEC, preferably taken in combination.

Examples of hydrogel compositions according to the invention that include xanthan gum (XANTHANE FNCSP-PC®) and/or HEC (NATROSOL 250HHX®) are shown in Table 1 below.

TABLE 1

| | | Formula No. | | | | |
|---|---|---|---|---|---|---|
| | | 190155.0168P/F1 | 190155.0173P/F1 | 190155.0174P/F1 | 190155.0175P/F1 | 190155.0176P/F1 |
| | PURIFIED WATER | QS | QS | QS | QS | QS |
| COMPOSITION | PROPYLENE GLYCOL | 20 | 20 | 20 | 20 | 20 |
| % (w/w) | PEG-400 SR | 10 | 10 | 10 | 10 | 10 |
| | KOLLIDON VA 64 | 1 | 1 | 1 | 1 | 1 |
| | XANTHAN FNCSP-PC | 0.5 | 1 | 0.75 | 0.5 | 0.5 |
| | NATROSOL 250HHX | — | — | — | 0.3 | 0.5 |
| | GLYCERINE | 4 | 4 | 4 | 4 | 4 |
| | BHA | 0.1 | 0.1 | 0.1 | 0.1 | 0.1 |
| | POLYSORBATE 80 SR | 1.5 | 1.5 | 1.5 | 1.5 | 1.5 |
| | KOLLICREAM OA | 0.1 | 0.1 | 0.1 | 0.1 | 0.1 |
| | PHENOXYETHANOL | 1 | 1 | 1 | 1 | 1 |
| | 10% CITRIC ACID SOLUTION | 0.44 | 1.161 | 0.981 | 0.65 | 0.312 |
| | pH | 4.5 | 4.23 | 4.14 | 4.26 | 4.72 |
| Properties | Viscosity | RV18-10 rpm (1 min) 499.2 cps (15.6%) | RV18-10 rpm (1 min) 1834 cps (57.3%) | RV18-10 rpm (1 min) 1066 cps (33.3%) | RV18-10 rpm (1 min) 1635 cps (51.1%) | RV18-10 rpm (1 min) 2768 cps (86.5%) |

A flexible mixed film is thus advantageously formed on the skin surface with the xanthan gum and/or HEC and the copolymer polyvinylpyrrolidone/vinyl Acetate (KOLLIDON VA 64®) in addition to the other non-volatile solvents, PG and PEG allowing the creation of a reservoir of brimonidine and preferably brimonidine tartrate, and thus slowing the precipitation of brimonidine and extending its period of action.

Preferably, the topical composition according to the invention also comprises a natural or synthetic antioxidant, or a free radical scavenger.

The antioxidant is preferably chosen from butylated hydroxyanisole (BHA), DL-tocopherol, butylhydroxytoluene (BHT), propaldehyde, palmitate ascorbate or glutathione, taken alone or in a mixture, preferably BHA and/or DL-tocopherol.

The antioxidant is preferably used in the hydrogel compositions according to the invention at a concentration of between 0.01% and 4.0% by weight of the total weight of the composition, more preferably between 0.1% and 1.0% w/w, and even more preferably 0.1%, for example BHA at 0.1% w/w and/or DL-tocopherol at 0.1% w/w.

Preferably, the composition according to the invention comprises the free radical sensor, preferably amifostine, at a concentration between 0.1% and 3% by weight of the total composition weight, for example 2.5% w/w.

Preferably, when the topical composition according to the invention comprises an antioxidant, it also comprises a polysorbate, preferably polysorbate 80 (TWEEN 80 SR®) and/or polyoxyethylenated hydrogenated castor oil 40 (KOLLIPHOR RH 40®).

Preferably, the topical composition according to the invention comprises less than 5% polysorbate, preferably polysorbate 80 (TWEEN 80 SRC)), by weight of the total weight of the composition, more preferably 1-1.5%, and even more preferably 1%, and/or less than 3% of polyoxyethylenated hydrogenated castor oil 40 by weight of the total weight of the composition, preferably 1% of polyoxyethylenated hydrogenated castor oil 40.

Preferably, the topical composition according to the invention also comprises oleyl alcohol (KOLLICREAM OA®) and vitamin E, taken alone or in combination.

The incorporation of a hydrophilic solvent phase with solvents that have hygroscopic, humectant and skin-conditioning properties, including PG and glycerine, helps improve the solubility of brimonidine tartrate in the stratum corneum and increase the water content within it.

The advantageous incorporation of antioxidants improves the stability of the active agent.

The hydrogel compositions according to the invention thus help improve and prolong the cutaneous administration of brimonidine tartrate and meet the needs of patients with adequate and prolonged local vasoconstriction and superior protection of both epidermis and dermis compared to oxygen-reactive types and inflammatory mediators.

Such compositions according to the invention are easy to apply and can be applied to potentially irritated skin.

They dry quickly, leaving minimal residue on the skin.

The topical compositions according to the invention have a pH of between 4.0 and 6.0, preferentially between 4.2 and 5.5, more preferentially between 4.3 and 5.0, and even more preferentially 4.5.

Another object of the invention relates to a hydrogel composition according to the invention for its use as a medicine.

Preferably, the hydrogel composition according to the invention is used for the prevention and/or treatment of damage caused by radiation, whether this radiation comes from photons or protons or is natural, therapeutic or accidental, including ultraviolet (UV), namely UVA and UVB which can cause sunburn, rays in the visible light range, infra-red radiation (IR), or even ionising radiation such as X-rays and alpha, beta, gamma or even proton beams.

More preferentially, the hydrogel composition according to the invention is used for the prevention and/or treatment of dermatitis caused by radiation, notably within a radiotherapy treatment, for example by X-rays or by protons.

EXAMPLES

The present invention will now be illustrated with the following examples.

Example 1: Measurement of Solubility Saturation in Pure Solvents

Method

Saturated solutions were prepared by adding an excess of drug substance to various solvents and storing the samples in sealed containers for 24 hours at room temperature with continuous stirring.

The majority of the samples were stirred using a magnetic stirrer; however, in the case of viscous samples (such as pure glycerine), the samples were stirred using a rotary mixer. The speed of the rotary mixer was adjusted to ensure proper mixing of the sample, this generally involving slower rotation speeds.

After the equilibration period, samples were centrifuged or filtered and the brimonidine tartrate was quantified using the Thermo Scientific Dionex U3000 UPLC-UV system. The chromatographic conditions are described below:

Column: Sunfire C18 150 mm×4.6 mm, 3.5 μm
Temperature of column: 40° C.
Volume injected: 5111
Flow: 0.8 ml/minute
UV detection: 246 nm

Results

The solubility saturation results for each solvent used independently, as determined by UPLC-UV, are summarised in Table 2.

TABLE 2

| Sample | Raw material | Max solubility % (w/w) |
|---|---|---|
| E2 | TRANSCUTOL ® | 0.05 |
| E3 | ARLASOLVE ® DMI | 0.01 |
| E4 | GLUCAM ™ E10 | 0.72* |
| E5 | GLUCAM ™ E20 | 0.88* |
| E6 | Na Pyrrolidone Carboxylate (AJIDEW L50 ®) | 0.06 |
| E7 | Propylene Carbonate | 0.01** |
| E8 | PEG-400 | 0.10 |
| E9 | Hexylene Glycol | 0.01 |
| A1 | DMSO | ≥8.5*** |
| L1 | WATER (value as per literature‡) | 3.4**** |
| | WATER (measured value) | 6.40 |
| L2 | Propylene glycol (value as per literature‡) | ~0.1**** |
| | Propylene glycol (measured value) | 0.56 |
| | Glycerine (GLY, 20 ml scintillation flask) | 1.61 |

*degradation peaks observed after re-injection T + 72 hours

**degradation peaks observed after re-injection T + 24 hours.

***visual solubility performed. Because of the high solubility observed, UPLC-UV analysis was not performed.

****Product Monograph: PrALPHAGAN ®, brimonidine tartrate, ophthalmic solution 0.2% w/v ‡Conditions not specified

Conclusion

From the results thus obtained, DMSO appears to be an excellent solvent for brimonidine tartrate. Saturation was not reached even after the addition of 8.5% w/w brimonidine tartrate.

Water appears to be the second best solvent; the salt form of the active probably facilitates its solubility in water.

Then, in descending order, come glycerine (GLY), glucams, propylene glycol (PG) and PEG-400.

The observed solubility for other solvents is significantly lower and does not provide a satisfactory result for solubility of brimonidine tartrate.

Interestingly, well-known solvents such as Transcutol and DMI appear to be much less effective solvents than glycerine or propylene glycol for brimonidine tartrate.

Example 2: Measurement of Solubility Saturation in Mixtures of Solvents

Method

Saturated solutions were prepared, incubated and measured as described in Example 1.

Results

The solubility saturation results for each solvent used independently, as determined by UPLC-UV, are summarised in Table 3.

TABLE 3

| Raw material mix | Max solubility % (w/w) |
|---|---|
| PG/PEG-400 (raw materials ratio: 20:10) | 0.45 |
| PG/PEG-400/GLY (20:10:5) | 0.66 |
| PG/PEG-400/PVP (20:10:1) | 0.45 |
| PG/PEG-400/GLY/PVP (20:10:5:1) | 0.72 |
| PG/PEG-400/GLY/PVP/Water (20:10:5:1:40) | 3.3 |

Conclusion

As expected, the non-aqueous mixtures of solvents appear to have a lower solubility power than the mixtures containing water.

Nevertheless, according to the results thus obtained, it appears that the non-volatile mixture containing PG/PEG-400/GLY/PVP (20:10:5:1) was able to solubilise approximately 22% of the active agent compared to the aqueous mixture PG/PEG-400/GLY/PVP/water (20:10:5:1:40). This indicates that the non-volatile polar components of an aqueous gel might have some ability to dissolve brimonidine tartrate on the skin surface and in the stratum corneum, into the residual formula, even after the water has evaporated.

If concentrations of 1% or 1.5% brimonidine tartrate are used, the active agent may be at around 30% or 50% saturation respectively, in the aqueous solvent phase of the primary formulation prior to application. However, when the formulation is applied to the skin surface, the water will evaporate relatively quickly.

The results obtained therefore appear advantageous in terms of physical stability of the formulation but not necessarily in terms of conventional skin distribution, and the thermodynamic activity would be relatively low.

Example 3: Measurement of Stability in Single Solvents and Preliminary Mixtures of Solvents The solvent combinations were prepared as described in Table 4. To facilitate evaluation, 0.1% brimonidine tartrate was added to each mixture. The samples were stored at room temperature, 40° C. and 50° C. for 1 month with sampling intervals of T=0 and T=1 month.

TABLE 4

Mixtures of solvents used to assess compatibility with brimonidine tartrate

| | Sample | | | | | | | | | |
|---|---|---|---|---|---|---|---|---|---|---|
| Raw materials | M1 | M2 | M3 | M4 | M5 (grams) | M6 | M7 | M8 | M9 | M10 |
| DMSO | 25.0 | 25.0 | | | | 25.0 | 25.0 | | 25.0 | |
| GLUCAM E10 | 12.5 | | 12.5 | 12.5 | | 12.5 | 12.5 | | 12.0 | 12.5 |
| GLUCAM E20 | | 25.0 | | | 25.0 | 25.0 | 25.0 | | 25.0 | 25.0 |
| GLYCERINE | 12.5 | 12.5 | 12.5 | 12.5 | 12.5 | | | | 12.0 | |
| TRANSCUTOL | | | 50.0 | 25.0 | 50.0 | | 25.0 | 50.0 | 25.0 | |
| WATER | 100.0 | 87.5 | 75.0 | 100.0 | 62.5 | 87.5 | 62.5 | 100.0 | 50.0 | 112.5 |
| TOTAL | 150.0 | 150.0 | 150.0 | 150.0 | 150.0 | 150.0 | 150.0 | 150.0 | 150.0 | 150.0 |

The compatibility data generated in this study are summarised in Table 5.

TABLE 5

Compatibility of brimonidine tartrate in mixtures of solvents following storage at room temperature, 40° C. and 50° C. for 1 month

| | | T0 | | | T1 M | | | | |
|---|---|---|---|---|---|---|---|---|---|
| Reference | INCI | pH | Active agent (% w/w) | RSD (%) | Storage temperature | pH | Active agent (% w/w) | RSD (%) | Recovery relative to T0 (%/T0) |
| M1 | DMSO (10%) | 4.63 | 0.1035 | 0.1 | RT | 4.7 | 0.1060 | 1.0 | 102.4% |
| | GLUCAM E10 (5%) | | | | 40° C. | 4.87 | 0.1050 | 7.4 | 101.4% |
| | GLYCERINE (5%) | | | | 50° C. | | 0.0970 | 1.4 | 93.7% |
| M2 | DMSO (10%) | 5.01 | 0.1044 | 0.9 | RT | 4.86 | 0.1010 | 1.4 | 96.7% |
| | GLUCAM E20 (10%) | | | | 40° C. | 4.92 | 0.0990 | 1.1 | 94.8% |
| | GLYCERINE (5%) | | | | 50° C. | | 0.0670 | 0.3 | 64.2% |
| M3 | GLUCAM E10 (5%) | 5.09 | 0.1036 | 0.2 | RT | 5.03 | 0.1030 | 1.2 | 99.4% |
| | GLYCERINE (5%) | | | | 40° C. | 5.14 | 0.1010 | 1.1 | 97.5% |
| | TRANSCUTOL (20%) | | | | 50° C. | | 0.0970 | 1.3 | 93.6% |
| M4 | GLUCAM E10 (5%) | 4.63 | 0.1013 | 0.3 | RT | 4.45 | 0.0990 | 2.1 | 97.7% |
| | GLYCERINE (5%) | | | | 40° C. | 4.76 | 0.0990 | 0.9 | 97.7% |
| | TRANSCUTOL (10%) | | | | 50° C. | | 0.0920 | 0.9 | 90.8% |
| M5 | GLUCAM E20 (10%) | 5.29 | 0.0999 | 0.1 | RT | 5.18 | 0.1040 | 3.6 | 104.1% |
| | GLYCERINE (5%) | | | | 40° C. | 5.49 | 0.0970 | 0.7 | 97.1% |
| | TRANSCUTOL (20%) | | | | 50° C. | | 0.0770 | 0.6 | 77.1% |
| M6 | DMSO (10%) | 5.42 | 0.1032 | 0.6 | RT | 5 | 0.1000 | 0.1 | 96.9% |
| | GLUCAM E10 (5%) | | | | 40° C. | 5.14 | 0.0920 | 0.5 | 89.1% |
| | GLUCAM E20 (10%) | | | | 50° C. | | 0.0450 | 0.2 | 43.6% |

TABLE 5-continued

Compatibility of brimonidine tartrate in mixtures of solvents following storage at room temperature, 40° C. and 50° C. for 1 month

| | | T0 | | | T1 M | | | | |
|---|---|---|---|---|---|---|---|---|---|
| Reference | INCI | pH | Active agent (% w/w) | RSD (%) | Storage temperature | pH | Active agent (% w/w) | RSD (%) | Recovery relative to T0 (%/T0) |
| M7 | DMSO (10%) | 5.86 | 0.1050 | 0.3 | RT | 5.87 | 0.1030 | 1.2 | 98.1% |
| | GLUCAM E10 (5%) | | | | 40° C. | 5.82 | 0.0990 | 0.9 | 94.3% |
| | GLUCAM E20 (10%) | | | | 50° C. | | 0.0900 | 2.9 | 85.7% |
| | TRANSCUTOL (10%) | | | | | | | | |
| M8 | TRANSCUTOL (30%) | 4.46 | 0.1036 | 0.1 | RT | 4.28 | 0.1030 | 2.3 | 99.4% |
| | | | | | 40° C. | 4.7 | 0.1010 | 0.8 | 97.5% |
| | | | | | 50° C. | | 0.0980 | 1.6 | 94.6% |
| M9 | DMSO (10%) | 5.93 | 0.0997 | 0.4 | RT | 5.93 | 0.0960 | 0.5 | 96.3% |
| | GLUCAM E10 (5%) | | | | 40° C. | 5.89 | 0.0940 | 0.5 | 94.3% |
| | GLUCAM E20 (10%) | | | | 50° C. | | 0.0900 | 0.3 | 90.3% |
| | GLYCERINE (5%) | | | | | | | | |
| | TRANSCUTOL (10%) | | | | | | | | |
| M10 | GLUCAM E10 (5%) | 4.83 | 0.1034 | 0.7 | RT | 4.67 | 0.1000 | 0.0 | 96.7% |
| | GLUCAM E20 (10%) | | | | 40° C. | 4.47 | 0.0960 | 0.7 | 92.8% |
| | | | | | 50° C. | | 0.0430 | 2.0 | 41.6% |

According to the results obtained, the mean values are between 99.36% and 101.45% with a relative standard deviation of less than 1%.

Solvent blends without Glucam E20 show the most favourable stability profile, while glycerine appears to improve stability. When Glucam E10 was included in the compositions at a concentration of 5%, the stability of brimonidine tartrate improved. Brimonidine tartrate measurement values tend to decrease as the Glucam concentration increases. The most stable mixture of solvents was obtained for M8 (30% Transcutol in water), then for M1 (10% DMSO, 5% Glucam E10 and 5% glycerine in water).

The data obtained indicate that using Glucam E10 and E20 increases the risk of brimonidine tartrate instability. On the other hand, transcutol, DMSO and glycerine show acceptable compatibility profiles.

Example 4: Evaluating the Skin-Whitening Effect of Various Solvents in Formulations According to the Invention In the formulation according to the invention, propylene glycol (PG), dimethyl sulfoxide (DMSO) and polyethylene glycol 400 (PEG-400) have been identified as solvents of interest for brimonidine tartrate.

The concentration of these solvents varied in different low-viscosity hydrogel formulations (Table 6), and skin whitening was evaluated using the skin whitening model. The choice of different concentrations for each solvent tested was based on solubility data and local tolerance considerations. For example, as DMSO is a better solvent than PG for brimonidine tartrate, a lower concentration was chosen to create more favourable thermodynamic activity in the residual formula.

In these sample hydrogel formulations, hydroxyethyl cellulose (HEC, Natrasol HHX) was used as the gelling agent.

TABLE 6

Compositions of low-viscosity hydrogel containing various quantities of PG, DMSO and PEG-400

| | Composition/Formula-batch no. | | | |
|---|---|---|---|---|
| | 19-0155.0058/F1 | 19-0155.0059/F1 | 19-0155.0060/F1 | 19-0155.0061/F1 |
| | Concept | | | |
| | Low-viscosity hydrogel | | | |
| | Size of batch (g) | | | |
| | 200 | 200 | 200 | 200 |
| | Justification of formula | | | |
| | 20% PG, 5% PEG-400, 0.5% HEC | 20% PG, 10% PEG-400, 0.5% HEC | 5% DMSO, 5% PEG-400, 0.5% HEC | 5% DMSO, 10% PEG-400, 0.5% HEC |
| Ingredients (INCI) | % w/w | | | |
| Brimonidine Tartrate | 1.5 | 1.5 | 1.5 | 1.5 |
| Purified water | 67 | 62 | 82 | 77 |
| Propylene Glycol | 20 | 20 | | |
| DMSO | | | 5 | 5 |
| Vegetable Glycerine 4810 | 4 | 4 | 4 | 4 |

TABLE 6-continued

Compositions of low-viscosity hydrogel containing various quantities of PG, DMSO and PEG-400

| Ingredients (INCI) | 19-0155.0058/F1 | 19-0155.0059/F1 | 19-0155.0060/F1 | 19-0155.0061/F1 |
|---|---|---|---|---|
| Concept | Low-viscosity hydrogel | | | |
| Size of batch (g) | 200 | 200 | 200 | 200 |
| Justification of formula | 20% PG, 5% PEG-400, 0.5% HEC | 20% PG, 10% PEG-400, 0.5% HEC | 5% DMSO, 5% PEG-400, 0.5% HEC | 5% DMSO, 10% PEG-400, 0.5% HEC |
| | % w/w | | | |
| PEG-400 | 5 | 10 | 5 | 10 |
| KOLLIDON VA 64 | 1 | 1 | 1 | 1 |
| Phenoxyethanol | 1 | 1 | 1 | 1 |
| NATROSOL 250 HHX (HEC) | 0.5 | 0.5 | 0.5 | 0.5 |
| NaOH Solution 10% | QS pH 4.5 | QS pH 4.5 | QS pH 4.5 | QS pH 4.5 |

Skin whitening scores are shown in graphic form in FIG. 1 (average of three repetitions), and the trends were used to interpret the data.

From the results thus obtained, it appears that the formulae containing PG generated a faster onset of action with higher peak whitening scores than the DMSO equivalents.

The best result was obtained with the formula containing 20% PG and 10% PEG-400 (19-0155.0059/F1), which produced the best skin whitening with rapid onset of action and extended duration of action. The skin whitening profile obtained with the 19-0155.0059/F1 formula shows the best balance in terms of speed of action, intensity and duration of skin whitening.

Example 5: Evaluating the Skin-Whitening Effect of Various Polymers in Formulations According to the Invention The effect of several formulation base ingredients on skin whitening was tested in different low-viscosity hydrogel formulations (Table 7). Also, the formulations tested all include xanthan gum which has advantages in terms of stability.

TABLE 7

Low-viscosity compositions 19-0155.0100/F1, 19-0155.0101/F1, 19-0155.0111/F1 and 19-0155.0112/F1

| Ingredient | 19-0155.0100/F1 | 19-0155.0101/F1 | 19-0155.0111/F1 | 19-0155.0112/F1 |
|---|---|---|---|---|
| Concept | Low-viscosity hydrogel | | | |
| Size of batch (g) | 200 | 200 | 100 | 100 |
| Justification of formula | Formula 059F1 + Xanthan (Xn) | Formula 100/F1 without NATROSOL or KOLLIDON | Formula 101/F1 + KOLLIDON | Formula 101F1 + KOLLIDON + 0.1% BHA + TWEEN 80 |
| | % w/w | | | |
| Brimonidine Tartrate | 1.5 | 1.5 | 1.5 | 1.5 |
| Purified water | 61.63 | 63.3 | 62.14 | 57.2 |
| Propylene Glycol | 20 | 20 | 20 | 20 |
| Vegetable Glycerine 4810 | 4 | 4 | 4 | 4 |
| PEG-400 | 10 | 10 | 10 | 10 |
| Xanthan Gum (Xn) | 0.2 | 0.2 | 0.2 | 0.2 |
| KOLLIDON VA 64 | 1 | 0 | 1 | 1 |
| NATROSOL 250 HHX | 0.5 | | | |

TABLE 7-continued

Low-viscosity compositions 19-0155.0100/F1, 19-0155.0101/F1, 19-0155.0111/F1 and 19-0155.0112/F1

| | Composition/Formula-batch no. | | | |
|---|---|---|---|---|
| | 19-0155.0100/F1 | 19-0155.0101/F1 | 19-0155.0111/F1 | 19-0155.0112/F1 |
| | Concept | | | |
| | Low-viscosity hydrogel | | | |
| | Size of batch (g) | | | |
| | 200 | 200 | 100 | 100 |
| | Justification of formula | | | |
| Ingredient | Formula 059F1 + Xanthan (Xn) | Formula 100/F1 without NATROSOL or KOLLIDON | Formula 101/F1 + KOLLIDON | Formula 101F1 + KOLLIDON + 0.1% BHA + TWEEN 80 |
| | % w/w | | | |
| Phenoxyethanol | 1 | 1 | 1 | 1 |
| Butylated hydroxyanisole | | | | 0.1 |
| TWEEN 80 | | | | 5 |
| NaOH Solution 10% | 0.17 | | 0.16 | |
| TOTAL | 100.00 | 100.00 | 100.00 | 100.00 |
| Macroscopic appearance T0 | Yellow gel, transparent, low viscosity | Yellow gel, transparent, low viscosity | Yellow gel, transparent, low viscosity | Yellow gel, transparent, low viscosity |
| T1 M 4° C. | — | Same as T0 | — | Same as T0 |
| T1 M RT | — | Same as T0 | — | Same as T0 |
| T1 M 40° C. | — | Same as T0 | — | Same as T0 |
| Microscopic appearance T0 | No crystals, no other points worthy of note | No crystals, no other points worthy of note | No crystals, no other points worthy of note | No crystals, no other points worthy of note |
| T1 M 4° C. | — | Same as T0 | — | — |
| T1 M RT | — | Same as T0 | — | — |
| T1 M 40° C. | — | Same as T0 | — | — |
| pH T0 | 4.6 | — | 4.73 | 4.4 |
| T1 M 4° C. | — | — | 4.60 | 3.94 |
| T1 M RT | — | — | 4.76 | 4.02 |
| T1 M 40° C. | — | — | 4.53 | 3.84 |
| Remarks | | | T = 3 M RT: GY4, 40° C.: GY3* | |

Figure 2:
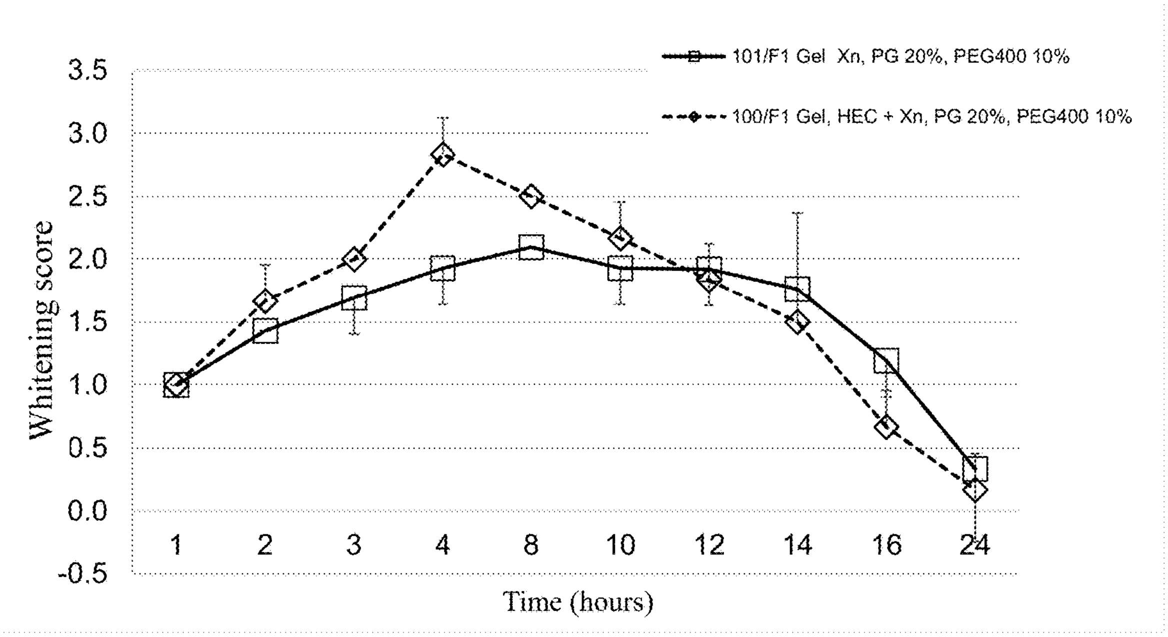
FIG. 2 represents the skin whitening scores obtained with various hydrogel compositions: 19-0155.0100/F1 and 19-0155.0101/F1.

On the basis of the results thus obtained and illustrated in FIG. 2, the two low-viscosity hydrogels tested produced acceptable skin whitening profiles. The same solvent system (20% PG+10% PEG-400) was used in each of the two compositions but the polymer combinations are different in that formula 19-0155.0100/F1 contains KOLLIDON VA-64®, NATROSOL HEC® and xanthan gum while formula 19-0155.0101/F1 contains only xanthan gum. Therefore, formula 19-0155.0100/F1 shows higher viscosity and greater skin adhesion after application than formula 19-0155.0101/F1.

There is a trend towards more pronounced whitening for formula 19-0155.0100/F1 formula and slightly longer whitening for formula 19-0155.0101/F1.

A significant difference between the compositions was observed in terms of organoleptic and drying time.

Formula 19-0155.0100/F1, which contains KOLLIDON VA-64®, NATROSOL HEC® and xanthan gum, although presenting slightly less pleasant sensory qualities by being a little stickier during application and requiring a longer drying time, allows prolonged duration of action and therefore a prolonged vasoconstrictor effect.

Example 6: Evaluating the Skin-Whitening Effect of Various Antioxidants in Formulations According to the Invention In the context of the development, it is essential to guarantee suitable chemical stability of the compositions according to the invention. pH is an important element in supporting chemical stability. Based on preliminary work and the natural pH of the skin, the targeted values were pH 4.0-5.5. Another important element is oxidation, and as a preliminary step to prevent or control oxidation, this involves screening for antioxidants.

The first step in the antioxidant selection process is to assess the physical compatibility of the antioxidants with formulations of interest. Many effective antioxidants are lipophilic in nature, for example butylhydroxyto-luene (BHT), butylhydroxyanisole (BHA), propyl gallate and tocopherol. As such, these components dissolve relatively easily or are retrospectively compatible with typical oil phases of emulsions. However, their hydrophobicity and low aqueous solubility make their incorporation into hydrogels more problematic and complicated. For the purposes of the preliminary tests, two antioxidants, BHA and tocopherol, were nevertheless more particularly screened in different formulations of hydrogels according to the invention.

BHA is a highly fat-soluble antioxidant widely used in both bulk oils and oil-in-water emulsions. BHA has been reported to possess antimicrobial activity and has demonstrated co-antioxidant activity via the regeneration of other antioxidants such as BHT and alpha-tocopherol. BHA is frequently used in combination with BHT and propyl gallate and with sequestrants or synergists such as citric acid.

Naturally occurring vitamin E is named RRR-alpha-tocopherol (commonly known as d-alpha-tocopherol); the synthetically produced form is all-rac-alpha-tocopherol (commonly known as dl-α-tocopherol). α-tocopherol is a lipophilic antioxidant and plays an important role in a wide range of biochemical and physiological processes; it has been selected as a proton donor. It has synergistic effects with vitamin C and other natural antioxidants. The effects of α-tocopherol have also been reported to regenerate in neutral and acidic environments.

Despite the presence of PG and PEG-400, potential solvents for lipophilic antioxidants, the use of one or more additional solubilisers could be advantageous. Two surfactants commonly used as solubilisers were screened: TWEEN 80® (polysorbate 80) and KOLLIPHOR RH40® (polyoxyethylene hydrogenated castor oil 40).

The compositions tested in this example are described in Table 8.

TABLE 8

Low-viscosity hydrogels containing antioxidants and a control substance were tested within a context of skin whitening

| | Composition/Formula-batch no. | | | | |
|---|---|---|---|---|---|
| | 19-0155.0111/F1 | 19-0155.0117/F1 | 19-0155.0121/F1 | 19-0155.0124/F1 | 19-0155.0125/F1 |
| | Concept: Low-viscosity hydrogel | | | | |
| | Size of batch (g) | | | | |
| | 100 | 100 | 100 | 100 | 100 |
| | Justification of formula | | | | |
| Ingredient | Formula 101F1 + KOLLIDON | Formula 101F1 + KOLLIDON + 0.1% BHA + 1% TWEEN 80 | Formula 101F1 + KOLLIDON + 0.1% BHA + 1.5% TWEEN 80 | Formula 111F1 + 0.1% Tocopherol + 1% KOLLIPHOR RH 40 | Formula 111F1 + 1% Tocopherol + 3% KOLLIPHOR RH 40 |
| | % w/w | | | | |
| Brimonidine Tartrate | 1.5 | 1.5 | 1.5 | 1.5 | 1.5 |
| Purified water | 62.14 | 61.0 | 60.43 | 61.02 | 58.09 |
| Propylene Glycol | 20 | 20 | 20 | 20 | 20 |
| Vegetable Glycerine 4810 | 4 | 4 | 4 | 4 | 4 |
| PEG-400 | 10 | 10 | 10 | 10 | 10 |
| Xanthan Gum | 0.2 | 0.2 | 0.2 | 0.2 | 0.2 |
| KOLLIDON VA 64 | 1 | 1 | 1 | 1 | 1 |
| Phenoxyethanol | 1 | 1 | 1 | 1 | 1 |
| Tween 80 | | 1 | 1.5 | | |
| BHA | | 0.1 | 0.1 | | |
| DL Tocopherol | | | | 0.1 | 1 |
| KOLLIPHOR RH40 | | | | 1 | 3 |
| NaOH Solution 10% | 0.16 | 0.2 | 0.27 | 0.18 | 0.21 |
| TOTAL | 100.00 | 100.00 | 100.00 | 100.00 | 100.00 |
| Macroscopic appearance T0 | Transparent gel, yellow, low viscosity | Transparent gel, yellow, low viscosity | Transparent gel, yellow, low viscosity | Transparent gel, yellow, low viscosity | Opaque gel, yellow, low viscosity |
| T1 M 4° C. | N/A | Same as T0 | N/A | Same as T0 | N/A |
| T1 M RT | N/A | Same as T0 | N/A | Same as T0 | N/A |
| T1 M 40° C. | N/A | Same as T0 | N/A | Slight increase in colour intensity | N/A |
| T2 M 4° C. | N/A | Same as T0 | Same as T0 | Same as T0 | N/A |
| T2 M RT | N/A | Same as T0 | Same as T0 | Same as T0 | N/A |
| T2 M 40° C. | N/A | Slight increase in colour intensity | Same as T0 | Same as T0 | N/A |
| T3 M 4° C. | N/A | Same as T0 | Less coloured than RT T3 M | Same as T0 | N/A |
| T3 M RT | N/A | Same as T0 | Same as T0 | Same as T0 | N/A |
| T3 M 40° C. | N/A | Same as T2 M 40° C. | More coloured than RT T3 M | Same as T0 | N/A |
| Microscopic appearance T0 | No crystals | No crystals | No crystals | No crystals | No crystals |
| T1 M 4° C. | N/A | N/A | N/A | Same as T0 | N/A |
| T1 M RT | N/A | N/A | N/A | Same as T0 | N/A |
| T1 M 40° C. | N/A | N/A | N/A | Same as T0 | N/A |
| T2 M 4° C. | N/A | Same as T0 | Same as T0 | Same as T0 | N/A |
| T2 M RT | N/A | Same as T0 | Same as T0 | Same as T0 | N/A |
| T2 M 40° C. | N/A | Same as T0 | Same as T0 | Same as T0 | N/A |
| T3 M 4° C. | N/A | Same as T0 | Same as T0 | Same as T0 | N/A |
| T3 M RT | N/A | Same as T0 | Same as T0 | Same as T0 | N/A |
| T3 M 40° C. | N/A | Same as T0 | Same as T0 | Same as T0 | N/A |

TABLE 8-continued

Low-viscosity hydrogels containing antioxidants and a control substance were tested within a context of skin whitening

| Ingredient | Composition/Formula-batch no. | | | | |
|---|---|---|---|---|---|
| | 19-0155.0111/F1 | 19-0155.0117/F1 | 19-0155.0121/F1 | 19-0155.0124/F1 | 19-0155.0125/F1 |
| | Concept | | | | |
| | Low-viscosity hydrogel | | | | |
| | Size of batch (g) | | | | |
| | 100 | 100 | 100 | 100 | 100 |
| | Justification of formula | | | | |
| | Formula 101F1 + KOLLIDON | Formula 101F1 + KOLLIDON + 0.1% BHA + 1% TWEEN 80 | Formula 101F1 + KOLLIDON + 0.1% BHA + 1.5% TWEEN 80 | Formula 111F1 + 0.1% Tocopherol + 1% KOLLIPHOR RH 40 | Formula 111F1 + 1% Tocopherol + 3% KOLLIPHOR RH 40 |
| | % w/w | | | | |
| pH T0 | 4.73 | 4.78 | 5.02 | 5.11 | 4.65 |
| T1 M 4° C. | 4.60 | 4.61 | N/A | 4.56 | N/A |
| T1 M RT | 4.76 | 4.61 | N/A | 4.65 | N/A |
| T1 M 40° C. | 4.53 | 4.61 | N/A | 4.58 | N/A |
| T2 M 4° C. | N/A | 4.80 | 5.19 | 4.56 | N/A |
| T2 M RT | N/A | 4.75 | 5.11 | 4.67 | N/A |
| T2 M 40° C. | N/A | 4.67 | 5.18 | 4.50 | N/A |
| T3 M 4° C. | N/A | 4.76 | 5.03 | 4.56 | N/A |
| T3 M RT | N/A | 4.67 | 4.98 | 4.65 | N/A |
| T3 M 40° C. | N/A | 4.61 | 5.18 | 4.59 | N/A |
| Remarks | Stability: AT: GY4, 40° C.: GY3 | Stability: 4° C. GY3, AT: GY3, 40° C.: GY2 | Stability: 4° C. GY2, AT: GY1, 40° C.: Significant increase in colour | Stability: 4° C. GY4, AT: GY3, 40° C.: GY2 | N/A |

Colour evaluation, using reference solutions standardized by Ph Eur (B, BY, Y, R, GY), was used to evaluate the colour of low-viscosity hydrogels. The active agent brimonidine tartrate gives a yellow colour that is pH dependent, and the clear gels provided a medium that facilitated colour assessment.

Also, the formulations proved sufficiently stable with only a few increments of colour intensity at 40° C. after 2-3 months.

The pH of the compositions is within the acceptable range of 4.5 to 5 even after 3 months of storage at 40° C.

According to the results thus obtained, all formulations that contain 0.1% BHA or 0.1% tocopherol are transparent.

However, formula 19-0155.0125/F1 is cloudy in appearance and this could be linked to the increased level of antioxidant (1% tocopherol) compared to the other compositions tested. The concentration of KOLLIPHOR RH40® must be increased in order to solubilise the high tocopherol load.

Even when the tocopherol content is reduced from 1% to 0.5%, the compositors show cloudiness (data not shown).

Finally, it was not possible to solubilise 1% BHA even with high concentrations of solubilisers.

Despite the challenges associated with solubilising high concentrations of tocopherol, formulation 19-0155.0125/F1 was also tested with the other compositions in Table 8 in the skin whitening model to assess the effect of 3% KOLLIPHOR RH40 ® and 1% tocopherol on skin whitening. It is important to note that all compositions thus tested in this example contain 20% PG, 4% glycerine, 10% PEG-400, 0.2% xanthan gum and 1% KOLLIDON VA 64®.

Figure 3:
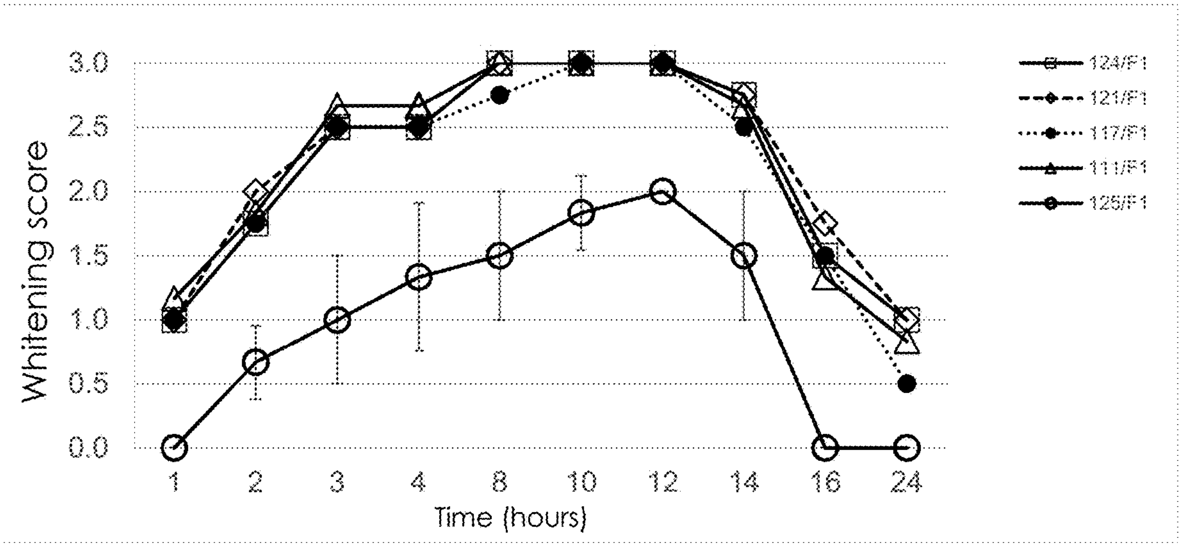
FIG. 3 represents the skin whitening scores obtained with various hydrogel compositions that may contain an antioxidant and a surfactant: 19-0155.0111/F1 (control; no antioxidant, no solubilising agent), 19-0155.0117/F1 (1% TWEEN 80 and 0.1% BHA), 19-0155.0121/F1 (1.5% TWEEN 80 and 0.1% BHA), 19-0155.0124/F1 (1% KOLLIPHOR RH40 and 0.1% DL Tocopherol) and 19-0155.0125/F1 (3% KOLLIPHOR RH40 and 1% DL Tocopherol).

The results obtained are shown in FIG. 3 (based on the mean of three replicates±standard deviation).

All formulations containing 0.1% BHA or 0.1% tocopherol and 1.5% or less TWEEN 80® or 1% KOLLIPHOR RH40® behaved in the same way as the so-called control formulation 19-0155.0111/F1. Each of these compositions exhibits similar skin-whitening profiles and achieves a maximum score of 3.0 over 2-4 hours. The speed of whitening activity is similar and acceptable, with scores of 2.0 or over after 3 hours. The duration of the effect is also very satisfactory, with skin-whitening scores between 0.5 and 1 at 24 hours. These compositions therefore offer an excellent skin-whitening performance.

Figure 4:
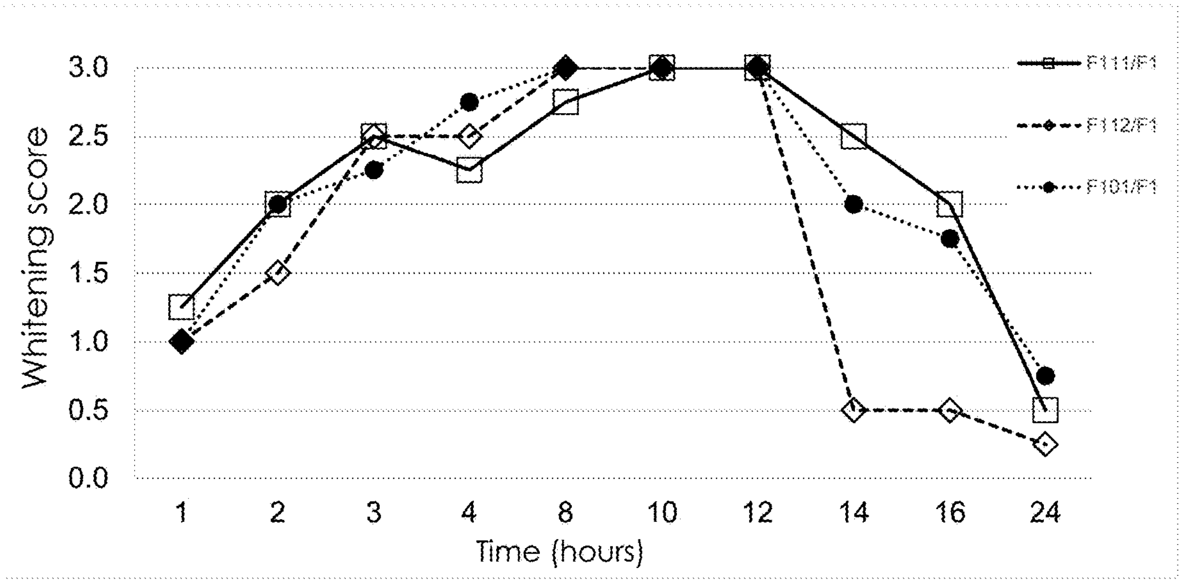
FIG. 4 represents the skin whitening scores obtained with various hydrogel compositions: 19-0155.0101/F1, 19-0155.0111/F1 and 19-0155.0112/F1.

On the other hand, formula 19-0155.0125/F1 behaves significantly less well than the other compositions, with a much slower onset, a lower peak and a shorter whitening time. In fact, the whitening returned to the baseline after 16 hours. It was hypothesized that the higher concentration of KOLLIPHOR RH40®, namely 3.0%, could be responsible for and indeed alter the thermodynamic activity and the release of brimonidine tartrate from the primary and/or residual composition. A similar effect on skin whitening was observed when 5% TWEEN 80 was used in combination with 0.1% BHA in formula 19-0155.0112/F1 (Table 7) as shown in FIG. 4.

According to the results thus obtained, concentrations of antioxidants less than or equal to 0.1% of BHA and of tocopherol can be advantageously incorporated into hydrogel compositions according to the invention comprising up to 1.5% of TWEEN 80® and up to 1% of KOLLIPHOR RH40® without physical instability or compromised appearance, intensity or duration of skin whitening.

When the concentration of KOLLIPHOR RH40® is increased to 3%, however, a marked reduction in skin whitening performance has been observed.

Example 7: Evaluation of the Effect on Skin Whitening of Various Compositions of Low-Viscosity Hydrogels Using an In Vivo Vasoconstriction Model The compositions and physical stability data of the low viscosity hydrogels tested are described in Table 9. These formulations are based on compositions 19.0155-0101 and 19.0155-0121 following positive stability and performance evaluations.

TABLE 9

| | Composition/Formula-batch no. | | |
|---|---|---|---|
| | 19-0155.0135/F1 | 19-0155.0134/F1 | 19-0155.0135P/F1 |
| | Concept | | |
| | Low-viscosity hydrogel | | |
| | Size of batch (g) | | |
| | 100 | 100 | 100 |
| | Justification of formula | | |
| | Formula 121/F1 + 1.5% TWEEN 80 SR | Formula 111/F1 + 1.5% TWEEN 80 SR | Formula 121/F1 vehicle + 1.5% TWEEN 80 SR |
| Ingredient | % w/w | | |
| Purified water | 60.49 | 60.54 | 62.01 |
| Vegetable Glycerine 4810 | 4 | 4 | 4 |
| Propylene Glycol | 20 | 20 | 20 |
| Brimonidine Tartrate | 1.5 | 1.5 | |
| Xanthan Gum | 0.2 | 0.2 | 0.2 |
| PEG-400 SR | 10 | 10 | 10 |
| BHA | 0.1 | | 0.1 |
| TWEEN 80 SR | 1.5 | 1.5 | 1.5 |
| DL Tocopherol | | | |
| KOLLIPHOR RH40 | | | |
| KOLLIDON VA 64 | 1 | 1 | 1 |
| KOLLIPHOR EL | | | |
| Phenox yethanol | 1 | 1 | 1 |
| 10% citric acid solution | | | 0.19 |
| 10% NaOH solution | 0.21 | 0.26 | |
| TOTAL | 100.00 | 100.00 | 100.00 |
| Stability data | | | |
| Macroscopic appearance T0 | Clear gel, yellow, low viscosity | Clear gel, yellow, low viscosity | Clear gel, colourless, low viscosity |
| Microscopic appearance T0 | No crystals, no other points worthy of note | No crystals, no other points worthy of note | No crystals, no other points worthy of note |
| pH T0 | 4.73 | 4.8 | 4.68 |

Each of the compositions was tested in triplicate using the in vivo vasoconstriction protocol as described below.

60 microlitres of each composition were applied once, blind and random manner at 8 a.m., to the upper chest, using a positive displacement pipette, on a 10-cm2 area defined using plastic O-rings.

Application, is followed by a 30-second massage, followed in turn by 10-minute post-application drying of the product.

Whitening scores on a conventional scale of 0 to 3 (3=maximum) are measured 1, 2, 3, 4, 8, 10, 12, 14, 16 and 24 hours after application.

Figure 5:
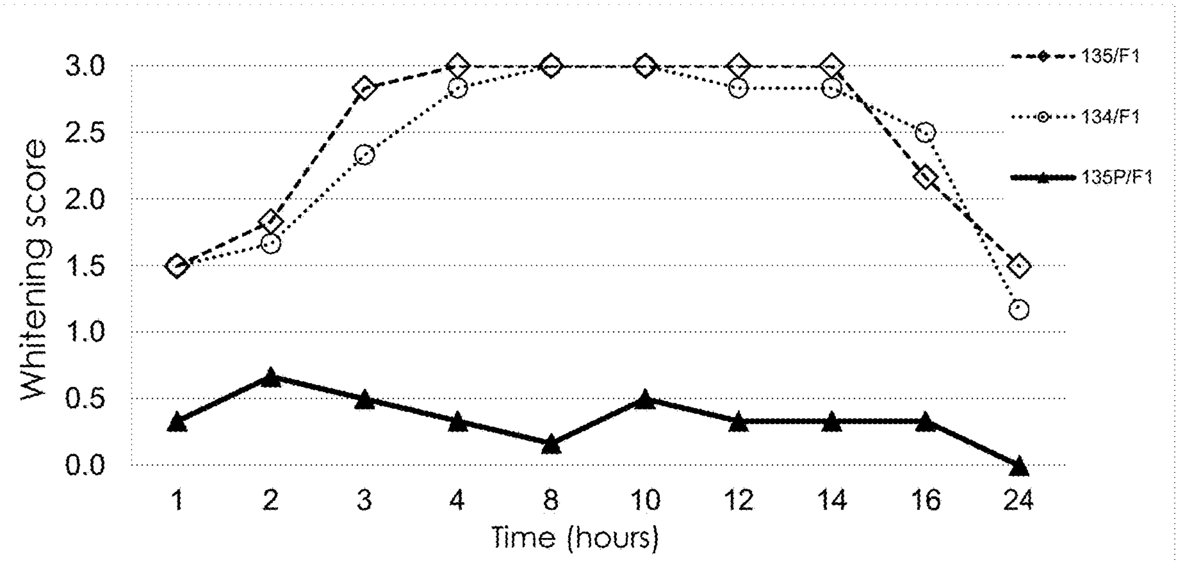
FIG. 5 represents the skin whitening scores obtained with various active hydrogel compositions (including brimonidine tartrate) or without active agent (containing only the vehicle).

The results thus obtained are illustrated in FIG. 5. On the basis of these results, formulations comprising 1.5% w/w brimonidine tartrate generate high levels of prolonged skin whitening indicative of vasoconstriction.

Both hydrogel formulations (19-0155.0135/F1 and 19-0155.0134/F1), generated similar vasoconstriction profiles. The degree of vasoconstriction is similar, about 1.5 after 1 hour and the maximum value after about 4 hours. Intensity of vasoconstriction remained at approximately 3.0 until 14 hours after application and reduced to 1.0-1.5 after 24 hours.

Example 8

Active compositions comprising brimonidine tartrate and vehicles listed in Table 10 were evaluated using the UV-induced erythema model.

The compositions were applied using the protocol as specified below. The process involves application in the evening before UV irradiation and 2 hours before UV irradiation, in three healthy volunteers.

Individual minimum erythemal doses (MED) for each subject were determined 24 hours before the experiment. Nine mini-zones were also delineated on the dorsal trunk of each subject, the compositions being applied at a dose of 5 mg/cm2 to these zones. The UV doses were administered and assimilated to 1×MED, (MED or DEM [minimal erythema dose]), 2×MED (2MED) and 3×MED (3MED).

An experimental reading was taken 24 hours after irradiation, using an investigator erythema score and Chroma Meter colorimeter.

TABLE 10

| Summary information on compositions tested using erythema induced by UV | | | | |
|---|---|---|---|---|
| Form of dose | Description | Principal properties | Formula No. | Reference No. |
| GEL | Low-viscosity hydrogel | Brimonidine tartrate 1.5% + BHA 0.1% + 1.5% TWEEN 80 SR | 19-0155.0135/F1 (see Table 9) | A |
| | | Formula Brimonidine Tartrate 1.5% + 1.5% TWEEN 80 SR | 19-0155.0134/F1 (see Table 9) | B |
| | | Vehicle | 19-0155.0134P/F1 (vehicle for formula 19-0155.0134/F1; no active agent brimonidine tartrate) | C |
| | | BHA 0.1% + 1.5% TWEEN 80 SR | 19-0155.0135P/F1 (see Table 9) | D |

Figure 6:
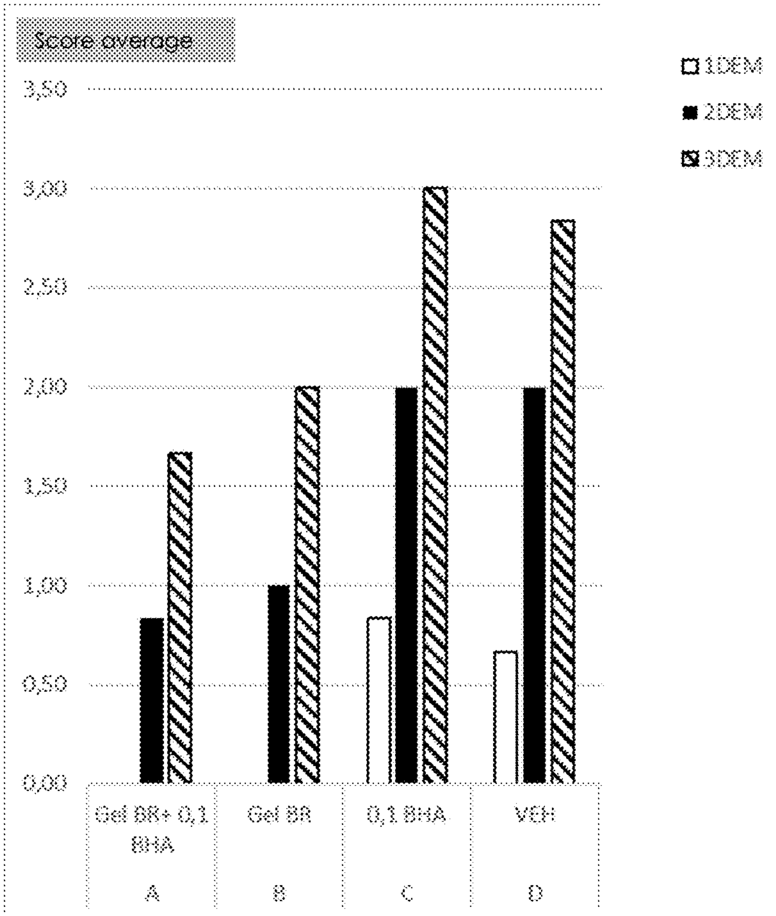
FIG. 6 represents the average erythema scores obtained with various active hydrogel compositions (including brimonidine tartrate) or without active agent (containing only the vehicle).

The mean erythema scores for each composition are summarized in FIG. 6.

Active compositions containing 1.5% brimonidine tartrate showed substantial reductions in erythema scores compared to the vehicles. Additional benefits in terms of anti-erythematous effects have been observed when 1.5% w/w brimonidine tartrate is combined with antioxidants. BHA and α-tocopherol were used as model antioxidants at concentrations of 0.1% and 1% w/w.

The hydrogel compositions according to the invention have demonstrated effective anti-erythematous properties in the UV-induced erythema model. When 1.5% w/w brimonidine tartrate was combined with antioxidants, BHA or α-tocopherol, additional benefits were observed in terms of treatment and/or prevention of erythema. The most potent anti-erythematous effects were observed when brimonidine tartrate was combined with 1.0% of each antioxidant.

Example 9: Performance Test—In Vivo Human Skin Whitening (Vasoconstriction) Model An in vivo vasoconstriction model was adapted to study and evaluate the performance of topical formulations according to the invention in terms of onset, magnitude and duration of effect.

Usually, the products are applied to the ventral part of the forearms and based on skin whitening, with an arbitrary score of 0, 1, 2 or 3 being assigned.

The tests performed involve the following step-by-step approach:

Implementation and calibration of the skin whitening model.

Effect of the applied quantity of each formulation tested

Effect of the brimonidine tartrate loading dose in the hydrogel formulations tested Effect of dosing frequency on skin whitening in the skin-whitening model Skin Whitening Test Methodology The parameters of the model used are described below.

Products applied randomly, application at 8 am

Application

Upper part of chest;

60 microlitres of formulation using a positive displacement pipette,

Surface area (10 $cm^2$) defined using plastic O-rings 30-second massage and 10-minute drying time after applying the product Evaluation 10 points in time for rating:

1, 2, 3, 4, 8, 10, 12, 14, 16 and 24 hours after application

Investigator's whitening score: scale of 0-3 (3=maximum)

Setting Up and Calibrating the Skin Whitening Test

In order to evaluate the performance (sensitivity, specificity and range) of the skin whitening model, several preliminary experiments were performed using the low viscosity hydrogel formulation base.

The preliminary experiments involved evaluation of:

The quantity of test item applied to the standardised test area, namely 60 μl, 30 μl and 15 μl per 10 cm2.

Variation in the loading dose of brimonidine tartrate, namely 1.5% w/w, 0.75% w/w, 0.25% w/w and 0.15% w/w Dosing frequency/dosing schedule Effect of Brimonidine-Tartrate Loading Dose in Hydrogel Test Articles in Skin Whitening Model The precise compositions used are described in Table 11.

TABLE 11

Low-viscosity hydrogel compositions (19-0155.0111/F1, 19-0155.0128/F1, 19-0155.0129/F1 and 19-0155.0130/F1) containing various concentrations of brimonidine tartrate; all formulations are based on the same reference formula, 111/F1

| | Composition/Formula-batch no. | | | |
|---|---|---|---|---|
| | 19-0155.0111/F1 | 19-0155.0128/F1 | 19-0155.0129/F1 | 19-0155.0130/F1 |
| | Concept | | | |
| | Low-viscosity hydrogel | | | |
| | Size of batch (g) | | | |
| | 100 | 100 | 100 | 100 |
| | Justification of formula | | | |
| | Formula 101/F1 + KOLLIDON | Formula 111/F1 + 0.75% Brimonidine | Formula 111/F1 + 0.25% Brimonidine | Formula 111/F1 + 0.15% Brimonidine |
| Ingredient | % w/w | | | |
| Brimonidine Tartrate | 1.5 | 0.75 | 0.25 | 0.15 |
| Purified water | 62.14 | 62.55 | 63.55 | 63.65 |
| Propylene Glycol | 20 | 20 | 20 | 20 |
| Vegetable Glycerine 4810 | 4 | 4 | 4 | 4 |
| PEG-400 | 10 | 10 | 10 | 10 |
| Xanthan Gum | 0.2 | 0.2 | 0.2 | 0.2 |
| KOLLIDON VA 64 | 1 | 1 | 1 | 1 |
| Phenoxyethanol | 1 | 1 | 1 | 1 |
| DL Tocopherol | | | | |
| KOLLIPHOR RH40 | | | | |
| NaOH Solution 10% | 0.16 | 0.19 | | |
| 10% citric acid solution | | 0.31 | | |
| TOTAL | 100.00 | 100.00 | 100.00 | 100.00 |
| Macroscopic appearance T0 | Yellow gel, transparent and fluid | Yellow gel, transparent and fluid | Fluid gel, transparent and colourless | Fluid gel, transparent and colourless |
| Microscopic appearance T0 | No crystals, no other points worthy of note | No crystals, no other points worthy of note | No crystals, no other points worthy of note | No crystals, no other points worthy of note |
| pH T0 | 4.73 | 5.55 | 4.29 | 4.43 |
| T1 M 4° C. | 4.60 | N/A | N/A | N/A |
| T1 M RT | 4.76 | N/A | N/A | N/A |
| T1 M 40° C. | 4.53 | N/A | N/A | N/A |
| Remarks | +3 M RT: GY4, 40° C.: GY3 | N/A | N/A | N/A |

Figure 7:
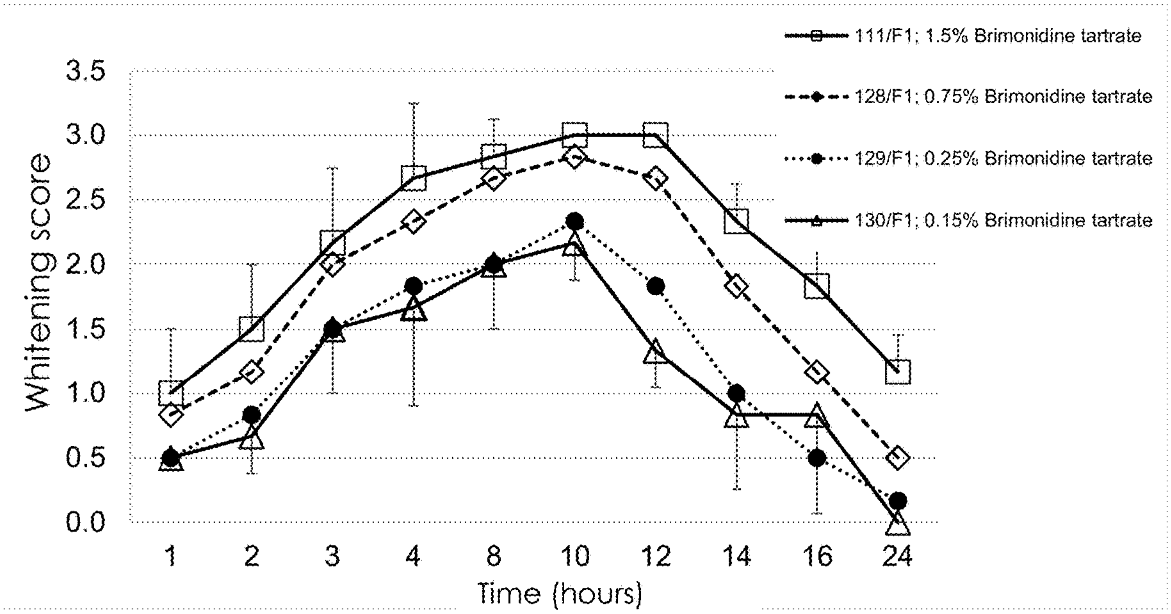
FIG. 7 represents the skin whitening scores obtained with the same hydrogel composition with variations in concentration of active agent (brimonidine tartrate 1.5%, 0.75%, 0.25% and 0.15% w/w).

The model was able to place the formulae in an appropriate order of rank with regard to brimonidine tartrate concentration (FIG. 7). The formulas were ranked in the following order, from highest to lowest whitening score:

1.5% brimonidine tartrate>0.75% brimonidine tartrate>0.25% brimonidine tartrate~=0.15% brimonidine tartrate.

This classification is equivalent to the following formulations:

19-0155.0111/*F*1>19-0155.0128/*F*1>19-0155.0129/*F*1~=19-0155.0130/*F*1

Formula 19-0155.0111/F1, containing 1.5% of brimonidine tartrate, is the only formula to reach the maximum skin whitening score of 3.0, and remained above 1.0 after 12 hours had elapsed.

Example 10: Performance of Reference Products in the Skin Whitening Model

The skin whitening model (vasoconstriction) was tested using reference pharmaceutical products known for bringing about skin whitening/vasoconstriction. The initial studies were carried out using:

MIRVAS 0 ® gel (0.5% w/w brimonidine tartrate)

Clobetasol propionate cream, 0.05% w/w

Norepinephrine hydrochloride solution (82 mg/ml in 70:30 ethanol:water) as used by Fahl (Effect of topical vasoconstrictor exposure upon tumoricidal radiotherapy. Int J Cancer; 135(4):981-988, 2014) and similar to the formulation used by Cleary et al. (Significant suppression of radiation dermatitis in breast cancer patients using a topically applied adrenergic vasoconstrictor. Radiation Oncology, 2017).

The skin whitening model allows differentiation of skin whitening capacity brought about by several active agents applied in different formulae in terms of appearance, intensity and duration of skin whitening.

The model shows adequate reproducibility and discrimination performance for the formulation screening phase.

Clobetasol Propionate Cream has been selected as a well-defined product/active agent involved in skin whitening. In fact, in vivo efficacy and bioequivalence of topical corticosteroids (1997 FDA guidance, https://www.fda.gov/media/70931/download) are assessed using this vasoconstriction effect.

Figure 8:
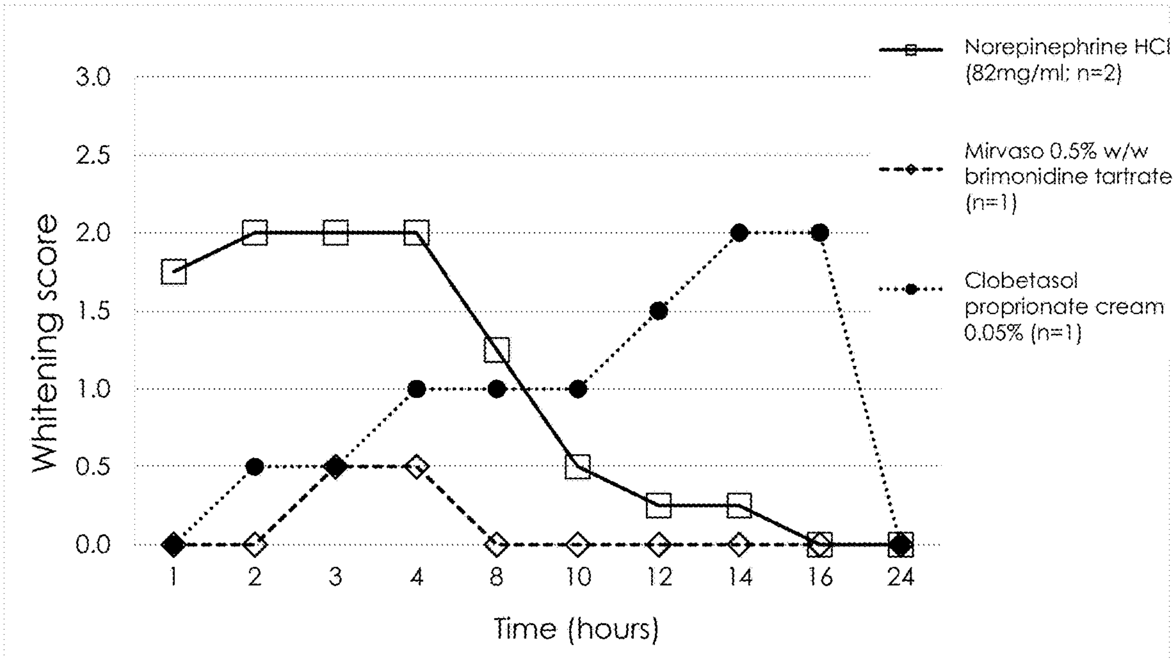
FIG. 8 represents the skin whitening scores obtained with reference vasoconstrictors.

Skin-whitening data for MIRVASO® gel, clobetasol propionate cream, 0.05% w/w and epinephrine HCl Solution (82 mg/ml in 70:30 ethanol:water) are shown in graphic form in FIG. 8.

MIRVASO® gel did not bring about significant whitening. This was expected as it was designed for application to relatively thin and sensitive facial skin for the treatment of rosacea. As a general rule, these products do not contain high concentrations of potential skin-penetrating agents because of the sensitivity of rosacea patients' skin. Additionally, facial skin is thinner than chest skin and thus has a lower barrier to penetration and permeation. The intensity and duration of action are insufficient to meet the desired demands of radiation-induced dermatitis.

Norepinephrine (noradrenaline) solution produced rapid and intermediate skin whitening 1 hour after application; however, the effect began to fade after the 4-hour observation interval. Whitening was at 0.5 or less after 10 hours and returned to baseline after only 16 hours. While the initial effects were promising, the duration and intensity of the effect are not sufficient.

Unlike the polar molecule norepinephrine and its aqueous ethanol vehicle, clobetasol propionate cream showed a slow onset of action with a gradual increase over 2 hours to a peak whitening score of 2.0 between 14 and 16 hours. There is a rapid reduction in whitening starting at 16 hours and returning to the baseline at 24 hours. The slower onset of action of clobetasol whitening may be related to the physical and chemical characteristics of the active agent, meaning that its lipophilic character results in reservoir formation and more limited distribution in the viable epidermis compared to the more hydrophilic norepinephrine. It is also important to note that the pharmacodynamic mechanisms of vasoconstriction are also different for clobetasol propionate and for norepinephrine.

Figure 9:
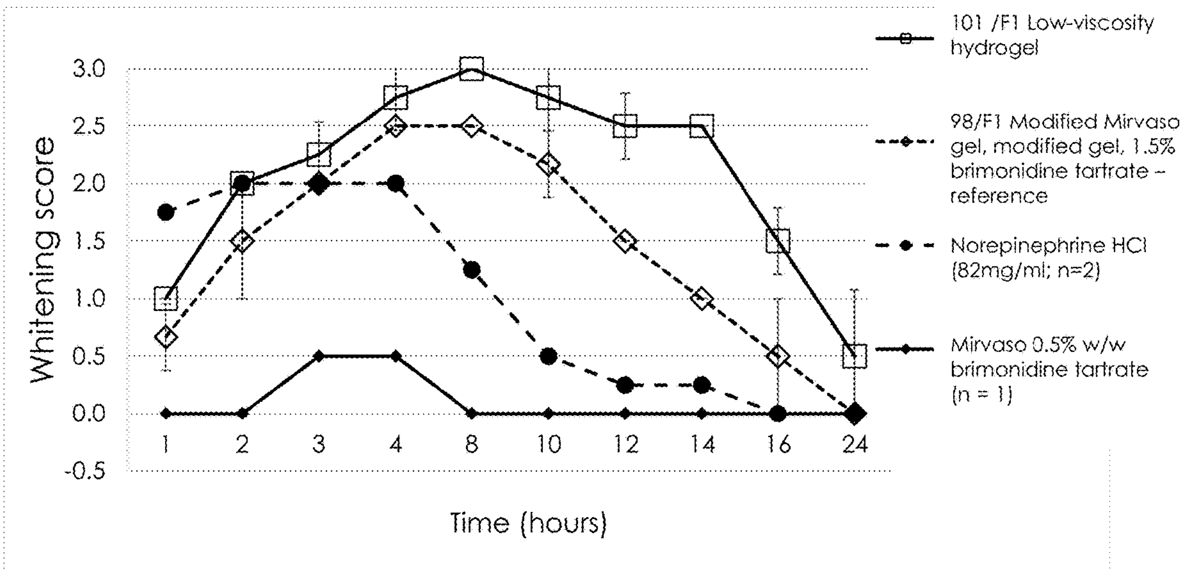
FIG. 9 represents the skin whitening scores obtained comparatively between a hydrogel composition according to the invention and a MIRVASO composition modified with 1.5% w/w of brimonidine tartrate (19-0155-0098/F1) and with a Norepinephrine solution and the MIRVASO® product (0.5% w/w of brimonidine tartrate).

Also, a modified MIRVASO-type formula was prepared with a high dose of 1.5% w/w of brimonidine tartrate (19-0155-0098/F1). This evaluation was conducted to assess the impact of an increased dose on skin whitening in a vehicle similar to MIRVASO. In the same experiment, a low-viscosity hydrogel composition according to the invention (19-0155-101/F1) was also tested at the same concentration. The corresponding skin whitening results for the two formulas are shown in FIG. 9. Norepinephrine solution and commercially available MIRVASO® gel (0.5% brimonidine tartrate) are also included for comparison.

The compositions thus tested are detailed in the table above.

The modified MIRVASO gel (1.5% Brimonidine tartrate 19-0155-0098/F1) brought about a substantial increase in the intensity and duration of skin whitening compared to the marketed MIRVASO® gel (0.5% of brimonidine tartrate).

However, the intensity of skin whitening did not persist for the desired long time to solve the technical problem according to the invention.

As well as this performance limitation, the MIRVASO vehicle is also unsuitable for radio-dermatitis. As previously indicated, the presence of titanium dioxide particles in the MIRVASO vehicle will interfere with and disrupt the dose of radiotherapy associated with the high-energy electromagnetic waves used.

Surprisingly, a low viscosity hydrogel formulation according to the invention (19-0155-101/F1) offered improved performance compared with the modified MIRVASO gel (1.5% brimonidine tartrate 19-0155-0098/F1) in terms of onset of action, peak effect and duration of action.

The low-viscosity hydrogel formulation according to the invention (19-0155-101/F1) demonstrated significant superiority of performance 8 hours after application (FIG. 9).

The reproducibility of the skin whitening model was demonstrated by the small standard deviation associated with the three replicates of formula 19-0155-101/F1 (FIG. 9, results presented as the mean of three replicates±standard deviation).

Example 11

This example is provided to demonstrate the advantages derived from increasing the concentration of xanthan gum in the hydrogel compositions according to the invention. The hydrogel formulation 19-0155.0163 contains 0.5% w/w xanthan gum, while the other formulations tested, 19-0155.0135/F1 and 19-0155.0111/F1, contain 0.2% w/w xanthan gum. The details of formulations 19-0155.0135/F1 and 19-0155.0111/F1 are shown in Tables 9 and 7 respectively, and formulation 19-0155.0163 is detailed in Table 12 below.

TABLE 12

| Ingredients | Composition/Formula-batch no. 190155.0163/20.00602 Concept Low-viscosity hydrogel Size of batch (g) 800 % w/w |
|---|---|
| PURIFIED WATER | QS |
| EDTA | 0.2 |
| SODIUM BENZOATE | 0.2 |
| SORBIC ACID | |
| PROPYLENE GLYCOL | 20 |
| PEG-400 SR | 10 |
| BRIMONIDINE TARTRATE | 1.5 |
| KOLLIDON VA 64 | 1 |
| XANTHAN FNCSP-PC | 0.5 |
| GLYCERINE | 4 |
| DL-ALPHA TOCOPHEROL | 0.1 |
| KOLLIPHOR RH40 | 1 |
| BUTYLHYDROXYANISOLE | |
| SR POLYSORBATE 80 | |
| PHENOXYETHANOL | |
| SOL ACID CITRIC 10% | |
| Sol NaOH 10% | 0.28 |

The stability data obtained for this formulation 190155.0163 are listed in Table 13 shown below.

TABLE 13

| | |
|---|---|
| Macroscopic appearance T0 | Slightly veiled yellow fluid gel: GY5 |
| T1 M 4° C./RT/40° C. | T1 M compliant GY4/compliant GY4/compliant GY4 |
| T2 M 4° C./RT/40° C. | T2 M compliant GY4/compliant GY4/slight colour change GY4-GY3 |
| T3 M 4° C./RT/40° C. | T3 M not compliant GY4- GY3/not compliant GY4- GY3/ colour change GY3 |
| Microscopic appearance T0 | Nothing significant |

TABLE 13-continued

| | |
|---|---|
| T1 M 4° C./RT/40° C. | T1 M NS/NS/NS |
| T2 M 4° C./RT/40° C. | T2 M NS/NS/NS |
| T3 M 4° C./RT/40° C. | T3 M NS/NS/NS |
| pH T0 | 4.43 |
| T1 M 4° C./RT/40° C. | T1 M 4.40/4.56/4.39 |
| T2 M 4° C./RT/40° C. | T2 M 4.59/4.51/4.58 |
| T3 M 4° C./RT/40° C. | T3 M 4.60/4.50/4.56 |
| Viscosity (RV mobile 34 - 6 rpm - 5 min) T0 | LV21, 50 rpm, 1 min: EEE; LV27, 12 rpm, 1 min: 1480 cP; 75.8% |
| T7J RT | T1 M LV27, 12 rpm, 1 min: 1850 cP; 74.0%/1822 cP; 72.9%/ 1755 cP; 70.2% |
| T2 M 4° C./RT/40° C. | T2 M LV27, 12 rpm, 1 min: 1875 cP; 75.0%/1837 cP; 73.4%/ 1702 cP; 68.1% |
| T3 M 4° C./RT/40° C. | T3 M LV27, 12 rpm, 1 min: 1852 cP; 74.1%/1822 cP; 72.9%/ 1702 cP; 68.2% |
| Colour T0 | GY5 |
| T1 M 4° C./RT/40° C. | T1 M GY4/GY4/GY4 |
| T2 M 4° C./RT/40° C. | T2 M GY4/GY4/GY4-GY3 |
| T3 M 4° C./RT/40° C. | T3 M GY4- GY3/GY4-GY3/GY3 |
| Remarks | Ph. Eur standard colour: GY5 |

The composition according to the invention comprising a higher concentration of xanthan gum (0.5% compared to 0.2% w/w, for example) is advantageous because the hydrogel is better retained at the site of application.

In general, increasing levels of viscosity-enhancing agents such as xanthan gum tend to reduce dermal release of the active agent from topically applied semi-solids.

Figure 10:
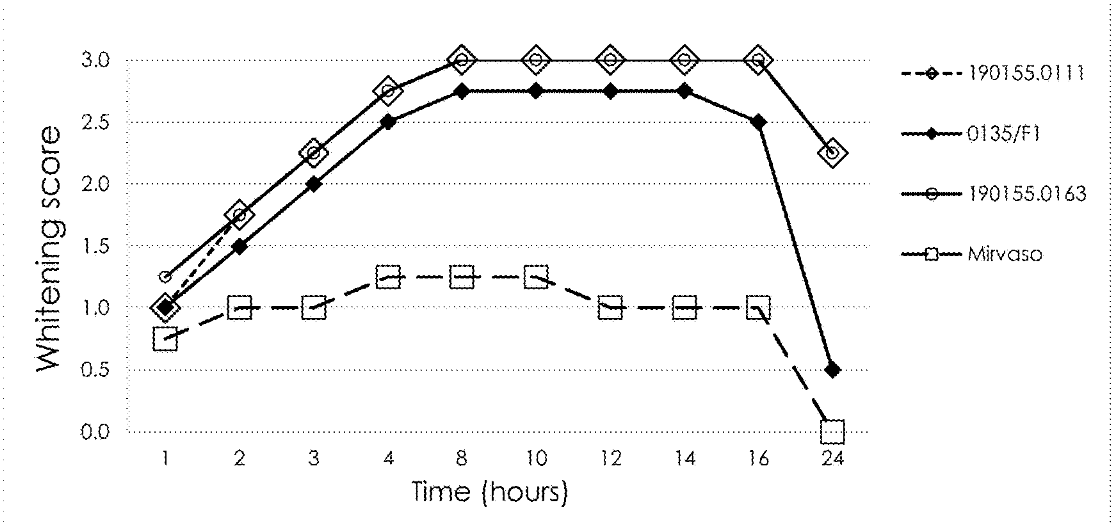
FIG. 10 represents the skin whitening scores obtained comparatively between a hydrogel composition according to the invention containing different concentrations of xanthan gum and the MIRVASO® product.

However, as illustrated by FIG. 10, according to the results obtained (average of 2 repetitions) on the skin whitening scores obtained comparatively between a hydrogel composition according to the invention containing different concentrations of xanthan gum and the MIRVASO® product, the composition according to the invention 190155.0163, comprising a xanthan gum concentration of 0.5%, produces the best result, comparable to that obtained with the same composition with 0.2% xanthan gum.

The invention claimed is:

1. A composition in a form suitable for topical administration comprising:
- a water base, and
- a vasoconstrictor chosen from brimonidine or salts thereof, wherein the vasoconstrictor is in a solvent-based phase comprising:
  - polyethylene glycol in combination with propylene glycol and/or dimethyl sulfoxide (DMSO);
  - a hydrophilic film-forming agent chosen from a polyvinylpyrrolidone/vinyl acetate copolymer, and/or polyvinylpyrrolidone in a non-crosslinked or acetate form; and
  - glycerine;

wherein the composition is in the form of a hydrogel.

2. The composition according to claim 1, wherein the hydrophilic film-forming agent is the polyvinylpyrrolidone/vinyl acetate copolymer.

3. The composition according to claim 1, further comprising a gel-forming agent chosen from xanthan gum and hydroxyethylcellulose (HEC), taken alone or in combination.

4. The composition according to claim 1, further comprising a natural or synthetic antioxidant or a free radical sensor.

5. The composition according to claim 4, wherein the antioxidant is chosen from the group consisting of butylated hydroxyanisole (BHA), DL-tocopherol, butylhydroxytoluene (BHT), propaldehyde, palmitate ascorbate or glutathione, and comobinations thereof.

6. The composition according to claim 4, wherein said antioxidant is present at a concentration of between 0.1% and 4.0% by weight of the total weight of the composition.

7. The composition according to claim 5, further comprising polysorbate and/or hydrogenated and polyoxyethylenated castor oil 40.

8. The composition according to claim 1, wherein the brimonidine or salts thereof is present at a concentration between 0.15% and 3.00% by weight of the total weight of the composition.

9. The composition according to claim 1, wherein the brimonidine or salts thereof is brimonidine tartrate.

10. The composition according claim 1, wherein the solvent-based phase comprises polyethylene glycol at a concentration of 10% by weight of the total weight of the composition, in combination with propylene glycol at a concentration of 20% by weight of the total weight of the composition.

11. The composition according to claim 1, further comprising oleyl alcohol and vitamin E, either alone or in combination.

12. The composition according to claim 4, wherein said antioxidant is present at a concentration of between 0.1% and 1.0% by weight of the total weight of the composition.

13. The composition according to claim 1, wherein the brimonidine or salts thereof is present at a concentration between 0.50% and 2.50% by weight of the total weight of the composition.

14. The composition according to claim 1, wherein the brimonidine or salts thereof is present at a concentration between 0.75% and 1.50% by weight of the total weight of the composition.

15. The composition according to claim 1, wherein the brimonidine or salts thereof is present at a concentration between 1.00% and 1.50% by weight of the total weight of the composition.

16. The composition according to claim 5, wherein the antioxidant is a combination of butylated hydroxyanisole (BHA) and DL-tocopherol.

17. A method of treating dermatitis caused by radiation from radiotherapy treatment, the method comprising:
- providing a composition according to claim 1 to a radiotherapy treatment patient in need thereof, and
- topically applying the composition to a radiotherapy treatment site of the patient.

* * * * *